US 12,085,645 B2

(12) United States Patent
Kyogoku

(10) Patent No.: US 12,085,645 B2
(45) Date of Patent: Sep. 10, 2024

(54) ULTRASONIC SENSOR, ULTRASONIC IMAGE GENERATING APPARATUS, AND ULTRASONIC DIAGNOSTIC APPARATUS

(71) Applicant: Hiroaki Kyogoku, Hyogo (JP)

(72) Inventor: Hiroaki Kyogoku, Hyogo (JP)

(73) Assignee: RICOH COMPANY, LTD., Tokyo (JP)

( * ) Notice: Subject to any disclaimer, the term of this patent is extended or adjusted under 35 U.S.C. 154(b) by 263 days.

(21) Appl. No.: 17/739,169

(22) Filed: May 9, 2022

(65) Prior Publication Data

US 2022/0381907 A1    Dec. 1, 2022

(30) Foreign Application Priority Data

May 31, 2021 (JP) ................. 2021-090947

(51) Int. Cl.
| B06B 1/02 | (2006.01) |
| A61B 8/00 | (2006.01) |
| G01S 7/52 | (2006.01) |
| G01S 15/89 | (2006.01) |

(52) U.S. Cl.
CPC ........ *G01S 15/8915* (2013.01); *A61B 8/4483* (2013.01); *B06B 1/0215* (2013.01); *G01S 7/52053* (2013.01); *B06B 2201/51* (2013.01); *B06B 2201/55* (2013.01); *B06B 2201/76* (2013.01)

(58) Field of Classification Search
CPC .............. B06B 1/0215; B06B 2201/51; B06B 2201/55; B06B 2201/76; A61B 8/4483
See application file for complete search history.

(56) References Cited

U.S. PATENT DOCUMENTS

| 10,258,311 B2 * | 4/2019 | Cho ..................... A61B 8/5207 |
| 2010/0141093 A1 * | 6/2010 | Fraser .................. B06B 1/0207 |
| | | 310/334 |
| 2016/0120515 A1 * | 5/2016 | Arai ..................... A61B 8/4483 |
| | | 600/443 |
| 2018/0028150 A1 * | 2/2018 | Kandori ............... B06B 1/0622 |

FOREIGN PATENT DOCUMENTS

| JP | 2019-076122 | 5/2019 |
| WO | WO2007/017775 | 2/2007 |
| WO | WO2015/009635 | 1/2015 |

* cited by examiner

*Primary Examiner* — Carolyn A Pehlke
(74) *Attorney, Agent, or Firm* — XSENSUS LLP

(57) ABSTRACT

An ultrasonic sensor includes an ultrasonic transducer; a first voltage output circuit to output a transmission voltage signal that oscillates between a first high voltage and a first low voltage, supplied to a first terminal of the ultrasonic transducer; a reception circuit to detect a voltage signal generated at a second terminal of the ultrasonic transducer; and the second voltage output circuit to output a second high voltage smaller than the first high voltage. The first voltage output circuit includes a first switching unit to perform switching between supplying the transmission voltage signal in ultrasonic transmission; and fixing a potential of the first terminal in ultrasonic reception. The second voltage output circuit includes a second switching unit that performs switching between supplying the second high voltage to the second terminal in ultrasonic transmission; and electrically separating the second voltage output circuit from the second terminal in ultrasonic reception.

12 Claims, 10 Drawing Sheets

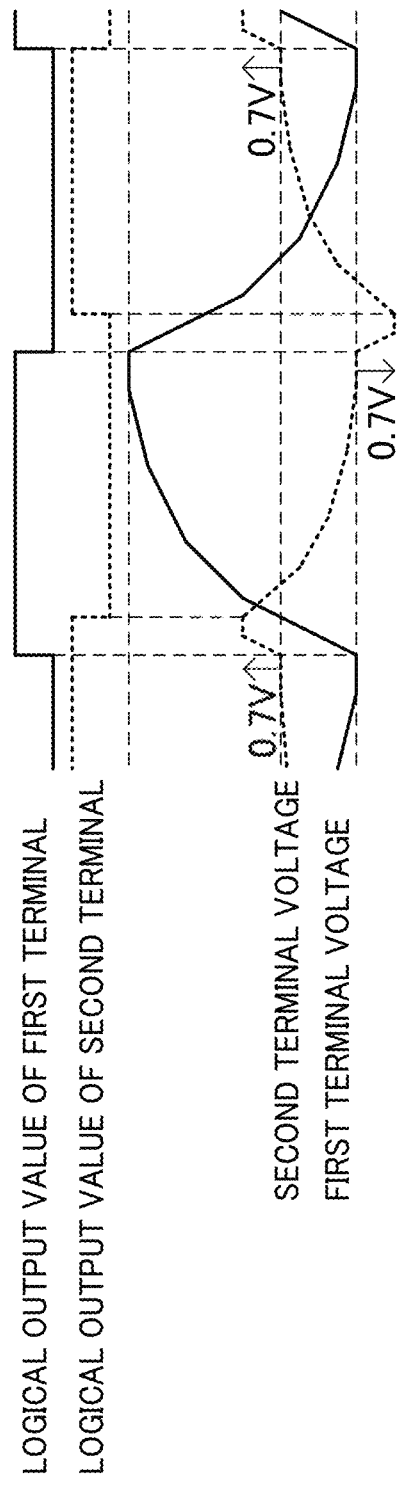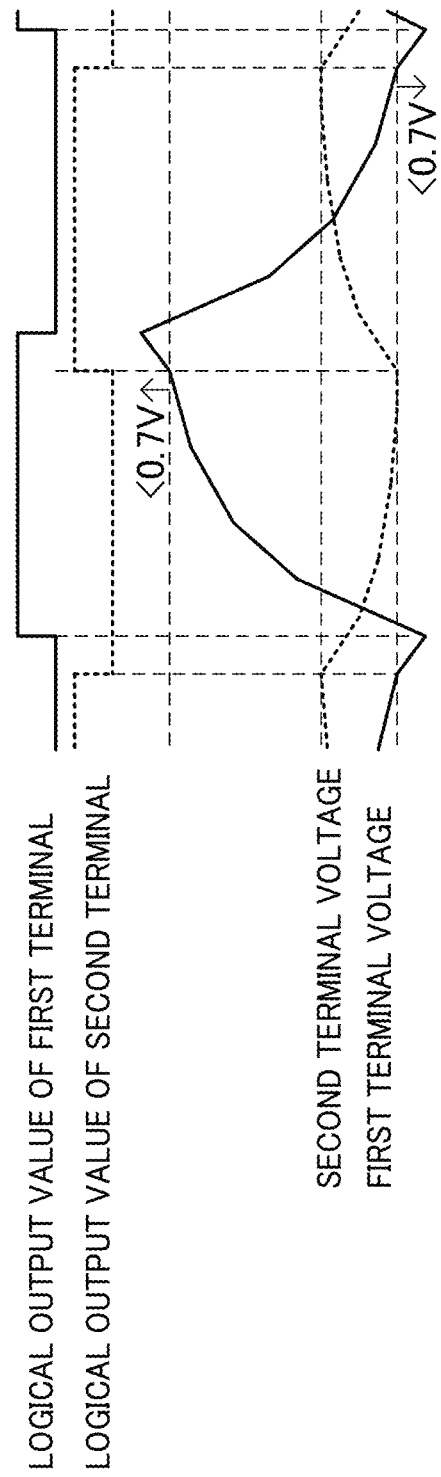

ULTRASONIC SENSOR, ULTRASONIC IMAGE GENERATING APPARATUS, AND ULTRASONIC DIAGNOSTIC APPARATUS

CROSS-REFERENCE TO RELATED APPLICATION

This patent application is based on and claims priority pursuant to 35 U.S.C. § 119(a) to Japanese Patent Application No. 2021-090947, filed on May 31, 2021, in the Japan Patent Office, the entire disclosure of which is hereby incorporated by reference herein.

BACKGROUND

Technical Field

Embodiments of this disclosure relate to an ultrasonic sensor, an ultrasonic image generating apparatus, and an ultrasonic diagnostic apparatus.

Related Art

There is known an ultrasonic sensor that supplies a transmission voltage signal to a first terminal of an ultrasonic transducer to transmit an ultrasonic wave from the ultrasonic transducer to an object, and receives the ultrasonic wave reflected by the object, so as to detect a reception voltage signal generated at a second terminal of the ultrasonic transducer.

SUMMARY

An embodiment provides an ultrasonic sensor that includes an ultrasonic transducer, a first voltage output circuit, a reception circuit, and a second voltage output circuit. The first voltage output circuit is connected to a first terminal of the ultrasonic transducer. The first voltage output circuit outputs a transmission voltage signal that oscillates between a first high voltage and a first low voltage lower than the first high voltage, in accordance with a transmission frequency. The transmission voltage signal is supplied to the first terminal of the ultrasonic transducer to control transmission of an ultrasonic wave from the ultrasonic transducer to an object. The first voltage output circuit includes a first switching unit that performs switching between supplying the transmission voltage signal output from the first voltage output circuit to the first terminal in ultrasonic transmission, and fixing a potential of the first terminal in ultrasonic reception. The reception circuit is connected to a second terminal of the ultrasonic transducer and detects a reception voltage signal generated at the second terminal by the ultrasonic wave reflected by the object. The second voltage output circuit is connected to the second terminal of the ultrasonic transducer. The second voltage output circuit outputs a second high voltage having a same polarity as a power supply voltage of the reception circuit, the second high voltage having an absolute value smaller than an absolute value of the first high voltage. The second voltage output circuit includes a second switching unit that performs switching between supplying the second high voltage to the second terminal in ultrasonic transmission, and electrically separating the second voltage output circuit from the second terminal in ultrasonic reception.

In another embodiment, an ultrasonic image generating includes the ultrasonic sensor described above; and an image processor configured to generate an image based on the reception voltage signal received by the reception circuit of the ultrasonic sensor.

In another embodiment, an ultrasonic diagnostic apparatus includes the ultrasonic sensor described above; and a display configured to display a shape of the object based on detection by the ultrasonic sensor.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 14 is a diagram illustrating voltages of first and second terminals of an ultrasonic transducer of the ultrasonic sensor in a case where switching of voltage applied to the second terminal is delayed from switching of voltage applied to the first terminal, as a comparative example;

FIG. 15 is a diagram illustrating switching timings of voltages applied to the second terminal of the ultrasonic transducer, according to the modification;

Figure 1:
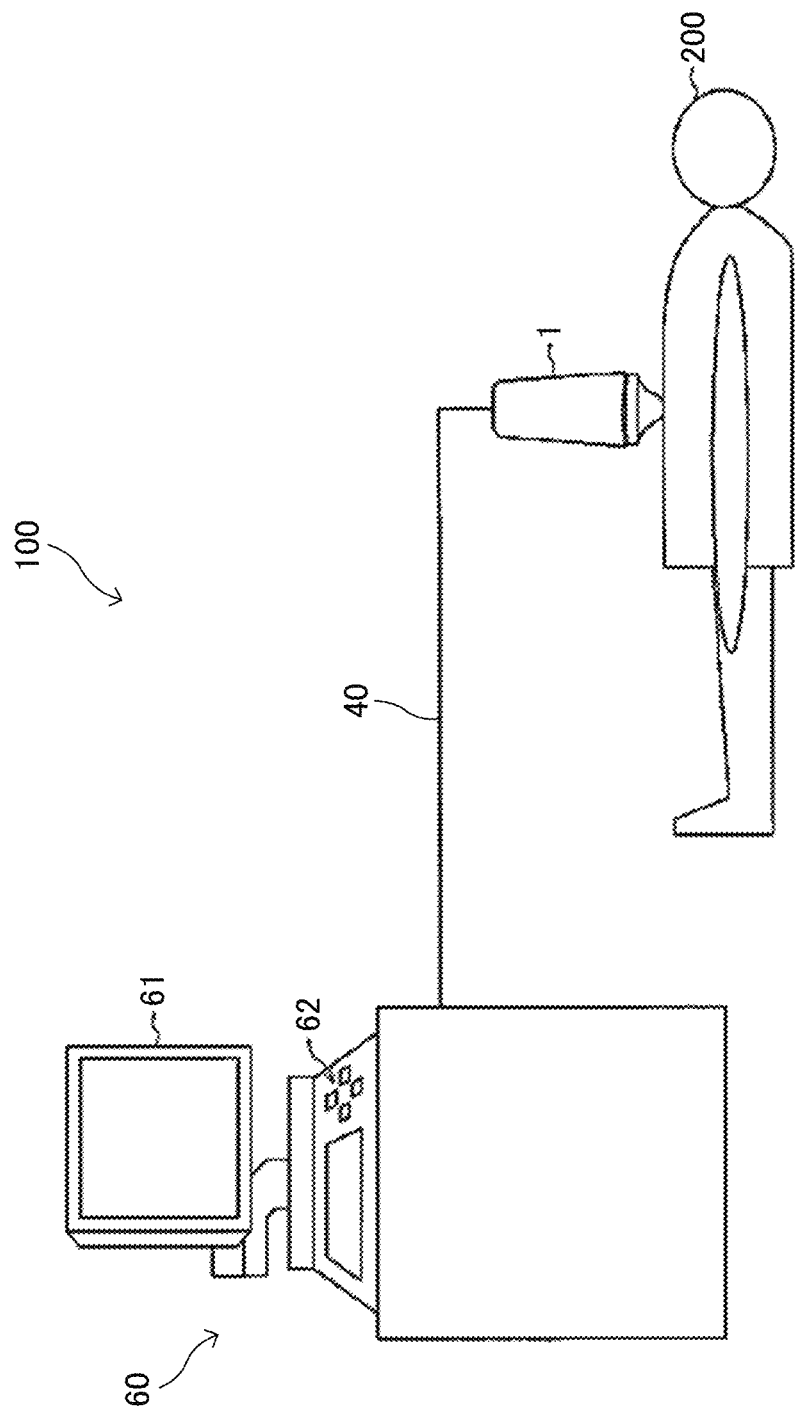
FIG. 1 is a schematic diagram illustrating an example of a configuration of an ultrasonic diagnostic apparatus according to one embodiment.

The accompanying drawings are intended to depict embodiments of the present invention and should not be interpreted to limit the scope thereof. The accompanying drawings are not to be considered as drawn to scale unless explicitly noted. Also, identical or similar reference numerals designate identical or similar components throughout the several views.

DETAILED DESCRIPTION

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Referring now to the drawings, embodiments of the present disclosure are described below. As used herein, the singular forms "a," "an," and "the" are intended to include the plural forms as well, unless the context clearly indicates otherwise.

Hereinafter, descriptions are given of an ultrasonic sensor according to an embodiment of the present disclosure. The ultrasonic sensor is used as an ultrasonic probe of an ultrasonic diagnostic apparatus.

Application of ultrasonic sensors according to embodiments is limited to an ultrasonic probe of an ultrasonic diagnostic apparatus, and application to various apparatuses is possible. Further, in the present embodiment, a human body is the subject of sensing, but the subject is not limited to a live subject such as a human body. The ultrasonic sensor according to the present embodiment is suitably used in an ultrasonic image generating apparatus used in a wide range of fields such as nondestructive inspection, underwater exploration, and personal authentication, but is also usable in an apparatus other than the ultrasonic image generating apparatus.

FIG. 1 is a schematic diagram illustrating an example of a configuration of an ultrasonic diagnostic apparatus according to the present embodiment.

In FIG. 1, an ultrasonic diagnostic apparatus 100 includes an ultrasonic probe 1. The ultrasonic probe 1 is an ultrasonic sensor that transmits an ultrasonic wave toward a subject 200 as an object to be sensed and receives an ultrasonic wave reflected from the subject 200. The ultrasonic diagnostic apparatus 100 further includes, in an apparatus body 60, a display 61 that visualizes and displays a signal (echo signal) output from the ultrasonic probe 1 and a control panel 62 that is operated by an operator.

Figure 2:
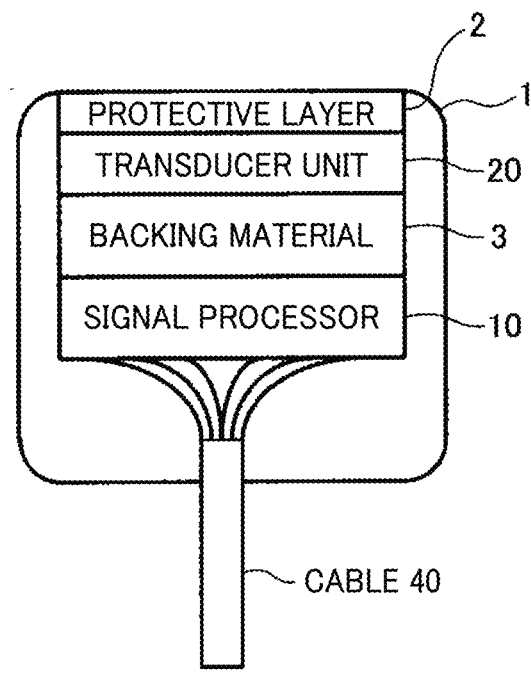
FIG. 2 illustrates an external configuration of an ultrasonic probe in the ultrasonic diagnostic apparatus illustrated in FIG. 1.

FIG. 2 illustrates a configuration of the ultrasonic probe 1.

The ultrasonic probe 1 includes a protective layer 2, a transducer unit 20, a backing material 3, and a signal processor 10.

The protective layer 2 protects the transducer unit 20. The protective layer 2 is preferably made of a material that does not give an unpleasant feeling to the subject 200 when the ultrasonic probe 1 is brought into contact with the subject 200 and has an acoustic impedance relatively close to that of a human body. As the protective layer 2, for example, flexible silicone rubber may be used.

The transducer unit 20 includes an array of ultrasonic transducers 21 (see FIG. 3) arrayed one dimensionally or two dimensionally. In the present embodiment, the ultrasonic transducers 21 are two dimensionally arrayed, and a three dimensional ultrasonic image is obtained. In the transducer unit 20, respective signal lines of the ultrasonic transducers 21 are connected to the signal processor 10.

The backing material 3 attenuates unnecessary vibration generated in the transducer unit 20.

The signal processor 10 performs generation of a transmission signal (transmission voltage signal) for transmitting an ultrasonic wave from the transducer unit 20, and processing of a reception signal (reception voltage signal) generated by the ultrasonic wave received by the transducer unit 20. The signal processor 10 is connected to the apparatus body 60 via a cable 40.

Figure 3:
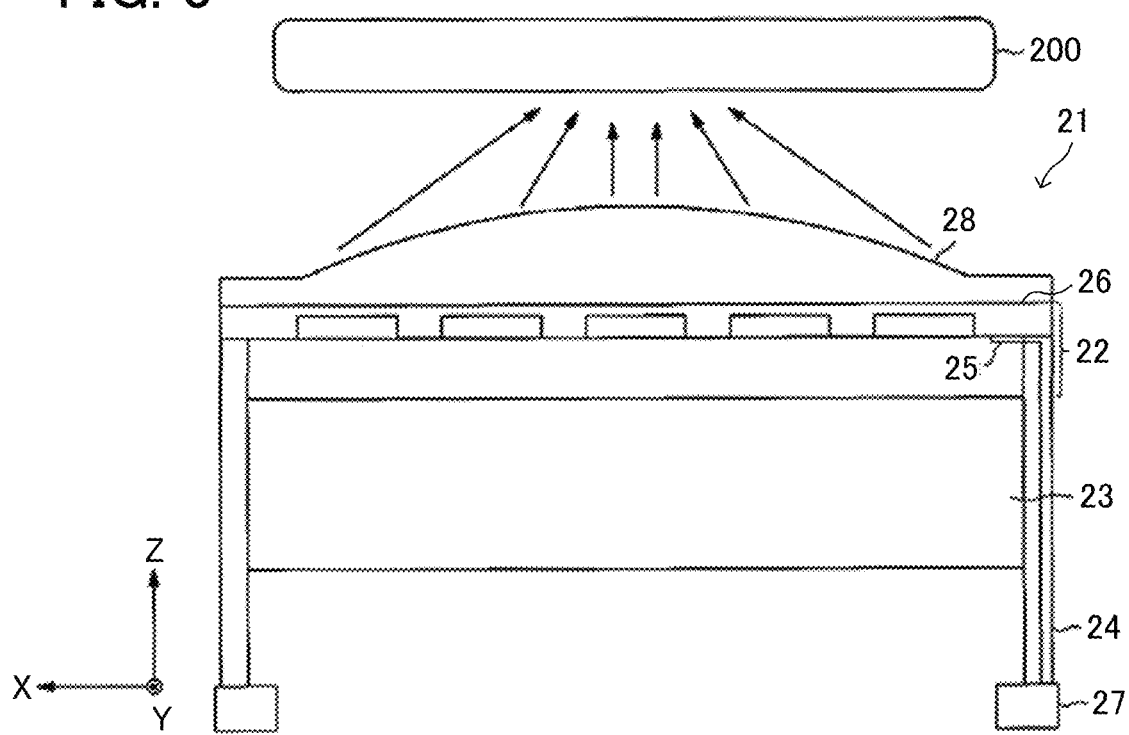
FIG. 3 is a schematic view of one ultrasonic transducer of a transducer unit of the ultrasonic probe illustrated in FIG. 1.

FIG. 3 is a schematic view of one ultrasonic transducer 21 of the transducer unit 20 of the ultrasonic probe 1.

As illustrated in FIG. 3, the ultrasonic transducer 21 includes a support plate 23 (a support), a piezoelectric micro-machined ultrasonic transducer (PMUT) chip 22 disposed on the support plate 23, a flexible board 24, wiring 25, a connector 27, and an acoustic lens 28. Although the ultrasonic transducer of the present embodiment uses a PMUT, alternatively, another ultrasonic transducer such as a capacitive micro-machined ultrasonic transducer (CMUT) may be used.

The PMUT chip 22 is connected to the connector 27 via the wiring 25 on the flexible board 24. The connector 27 is connected to a circuit board of the signal processor 10. The support plate 23 supports the PMUT chip 22 and functions as the backing material 3.

As the acoustic lens 28, for example, an acoustic lens made of silicone resin is suitably used. The acoustic lens 28 functions as the protective layer 2. The acoustic lens 28 focuses the ultrasonic wave transmitted from the PMUT chip 22 at a measurement position of the subject 200. The acoustic lens 28 has a shape (so-called a dome shape) in which a central area is thicker than a peripheral area. The acoustic lens 28 contacts the subject 200 and deforms, thereby tightly contacting the subject 200. Then, acoustic lens 28 artificially refracts ultrasonic waves to converge by a difference in propagation speed of the ultrasonic waves, caused by a difference in thickness between the central area and the peripheral area.

The acoustic lens 28 and the PMUT chip 22 are bonded to each other by an adhesive 26 as an adhesive layer. The adhesive 26 used for bonding the acoustic lens 28 and the PMUT chip 22 is preferably an adhesive of a silicone-based resin, and preferably has a relatively thin thickness of 20 μm or less.

Figure 4:
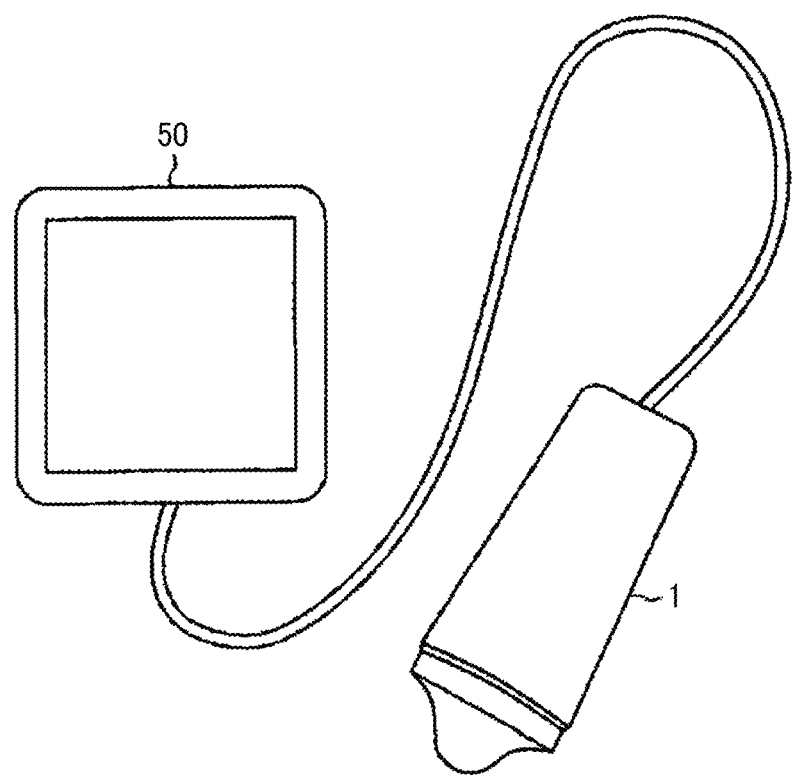
FIG. 4 is a schematic diagram illustrating a configuration of an ultrasonic diagnostic apparatus according to another embodiment.

As illustrated in FIG. 4, an ultrasonic diagnostic apparatus according to another embodiment includes a display terminal 50 as a display unit and the ultrasonic probe 1 connected to the display terminal 50 by a cable.

Figure 5:
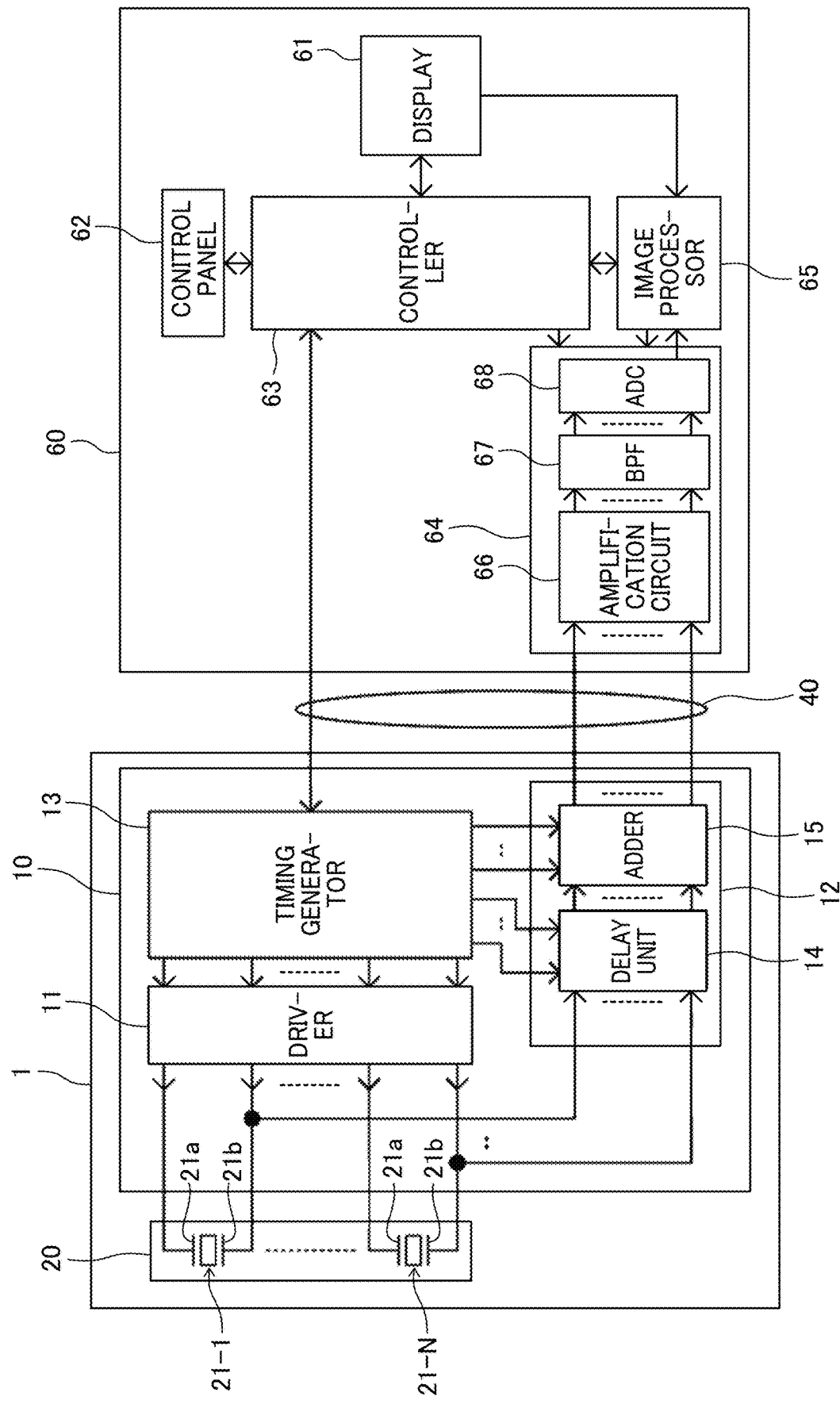
FIG. 5 is a block diagram illustrating an example of a configuration of the ultrasonic diagnostic apparatus according to one embodiment.

FIG. 5 is a block diagram illustrating an example of a configuration of the ultrasonic diagnostic apparatus according to the present embodiment.

The apparatus body 60 is connected to the ultrasonic probe 1 via the cable 40. The apparatus body 60 transmits a transmission signal (transmission voltage signal) to the ultrasonic probe 1 via the cable 40, thereby causing the ultrasonic probe 1 to transmit ultrasonic waves. Further, the apparatus body 60 receives, from the ultrasonic probe 1, a reception signal (reception voltage signal) generated based on the received ultrasonic wave by the ultrasonic probe 1, thereby visualize the internal state of the subject 200 as an ultrasonic image.

The apparatus body 60 of the present embodiment includes the display 61, the control panel 62, a controller 63, a signal converter 64, and an image processor 65 as an image generation unit.

The display 61 includes a monitor such as a liquid crystal display (LCD) and displays an image generated by the image processor 65.

The control panel 62 receives, for example, an instruction operation for instructing start of diagnosis, an input operation for inputting information related to the subject 200. The control panel 62 includes, for example, an operation panel or a keyboard.

The controller 63 controls operation of the ultrasonic diagnostic apparatus 100. The controller 63 may be implemented by a general-purpose computer. In particular, the controller 63 is connected to the signal processor 10 of the ultrasonic probe 1. The controller 63 transmits timing information to a timing generator 13 of the signal processor 10 via the cable 40. The timing information is for generating operation timings of a driver 11 and a reception circuit 12 (a delay unit 14 and an adder 15).

The signal converter 64 receives a reception output signal (an output signal of the reception circuit 12) from the reception circuit 12 of the ultrasonic probe 1 via the cable 40. The signal converter 64 performs signal processing on the received output signal with an amplification circuit 66, a band pass filter (BPF) 67, and an analog-to-digital (A/D) converter 68, and outputs the processed signal to the image processor 65. To be specific, in the signal converter 64, the amplification circuit 66 amplifies the output signal that is weak, and the BPF 67 cuts noise in a low frequency band and a high frequency band. Then, the A/D converter 68 performs A/D conversion for converting the output signal (an analog signal) into a digital signal. Thus, the signal converter 64 outputs, as digital data, the reception output signal received from the ultrasonic probe 1 to the image processor 65.

All or a part of the signal converter 64 may be included in the signal processor 10 of the ultrasonic probe 1.

Under the control of the controller 63, the image processor 65 generates an image for ultrasonic diagnosis (ultrasonic image) representing the internal state of the subject 200, using the output signal (digital data) received from the signal converter 64. The image processor 65 may be implemented by processing by a central processing unit (CPU) or a processing circuit such as a graphics processing unit (GPU).

The ultrasonic probe 1 is connected to the apparatus body 60 via the cable 40, and includes the transducer unit 20 and the signal processor 10. As illustrated in FIG. 5, the signal processor 10 includes the timing generator 13, the driver 11, and the reception circuit 12 including the delay unit 14 and the adder 15.

The timing generator 13 controls timing of each operation of the driver 11 and the reception circuit 12 (the delay unit 14 and the adder 15) based on the timing information from the controller 63 of the apparatus body 60. Specifically, the timing generator 13 performs timing control for the driver 11 to apply transmission signals to the ultrasonic transducers 21 with time differences corresponding to individual distances thereto, so that ultrasonic waves transmitted from the ultrasonic transducers 21 disposed at different positions simultaneously arrive at one point of the subject 200. Hereinafter, a suffix indicating an arrangement number is added to the reference numeral of the ultrasonic transducer 21, and the ultrasonic transducer 21 may be referred to as, for example, a transducer 21-1 or 21-N (N=the number of the ultrasonic transducers 21).

In addition, there are differences in arrival times at which the ultrasonic waves reflected by the subject 200 reach the ultrasonic transducers 21-1 to 21-N disposed at different positions. Accordingly, for the reception circuit 12, the timing generator 13 performs timing control to correct the arrival time differences. Specifically, when the distance is short, reflected ultrasonic waves reach the ultrasonic transducer 21 in a short time. Accordingly, the delay unit 14 provides a predetermined delay time to the reception signal of the ultrasonic transducer having a shorter distance. The adder 15 adds the reception signals of the ultrasonic transducers 21-1 to 21-N and transmits the addition result as a reception output signal to the signal converter 64 of the apparatus body 60 via the cable 40.

Figure 6:
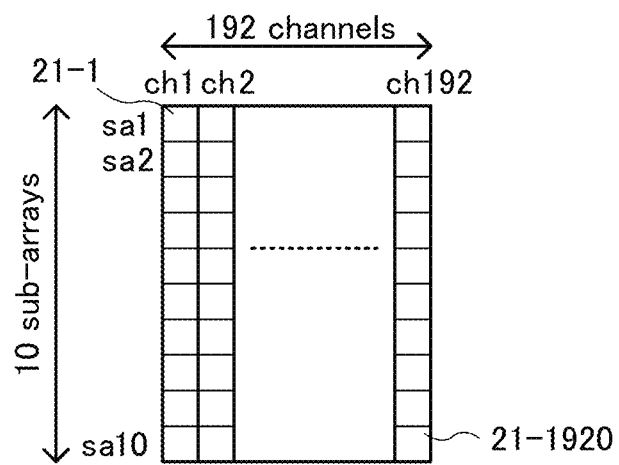
FIG. 6 illustrates an example of an array of ultrasonic transducers of the ultrasonic probe according to one embodiment.

In the present embodiment, for example, as illustrated in FIG. 6, the ultrasonic transducers 21 are arranged in a two dimensional array of 192 horizontal lines (channels ch1 to ch192) and 10 vertical lines (sub-arrays sa1 to sa10). In this case, the reception circuit 12 receives 1920 reception signals from the ultrasonic transducers 21-1 to 21-1920. The reception circuit 12 performs, for each of the channels ch1 to ch192, delay addition processing on reception signals from 10 ultrasonic transducers 21 on the sub-arrays sa1 to sa10 to be aggregated into one piece of information. Thus, the reception circuit 12 transmits information of the channels ch1 to ch192 as 192 pieces of information to the signal converter 64 via the cable 40. Note that a signal amplification unit may be provided in a preceding stage of the delay unit 14.

Preferably, the distance between the driver 11 and the reception circuit 12 and each of the ultrasonic transducers 21-1 to 21-N is as short as possible. This is for reducing ringing due to wiring between the driver 11 and each of the ultrasonic transducers 21-1 to 21-N and voltage drop due to the wiring, and for inhibiting a decrease in signal-to-noise (S/N) ratio caused by external noise with respect to wiring between the reception circuit 12 to each of the ultrasonic transducers 21-1 to 21-N. Preferably, the signal processor 10 is constructed of one integrated circuit (IC) and is disposed in the vicinity of the transducer unit 20, to secure high-speed communication of, for example, 10 MHz to 100 MHz in communication from the timing generator 13 to the driver 11 and the reception circuit 12.

In general, in an ultrasonic sensor such as the ultrasonic probe 1, increasing the frequency of an ultrasonic wave is preferred for the purpose of increasing the resolution of an ultrasonic image. However, increasing the frequency of the ultrasonic wave results in attenuation of the ultrasonic wave in the object (the subject 200) subjected to the ultrasonic wave. Accordingly, it is preferred to transmit a stronger ultrasonic wave. Therefore, it is preferred to apply a stronger transmission signal to the ultrasonic transducer 21.

In order to obtain a two dimensional image or a three dimensional image of an object by an ultrasonic sensor such as the ultrasonic probe 1, a delay circuit (the delay unit 14) corresponding to a distance (arrival time) from the ultrasonic transducer 21 to the object, an addition circuit (the adder 15) for adding reception signals of the plurality of ultrasonic transducers 21, and the like are used. Therefore, when the frequency of the ultrasonic wave is increased, it is necessary to increase the speed of the circuit operation of the delay circuit, the addition circuit, and the like.

For example, assume that the delay circuit (the delay unit 14) is a sample-and-hold circuit including a switch and a capacitor, and the reception voltage signal of the 10 MHz is sampled eight times in one cycle. In this example, the operation frequency is as high as 80 M samples per second. When the sample-and-hold signal of 10 MHz is amplified 10 times by the addition circuit (the adder 15), the bandwidth of the operational amplifier used for signal amplification should be equal to or greater than 1 GHz. Thus, both are high-speed operations. In order to realize such a high frequency bandwidth by an integrated circuit, a fine semiconductor element is used. Since each node of a fine semiconductor element has a low withstand voltage, the power supply voltage of the reception circuit 12 (the delay unit 14 and the adder 15) is lowered.

In an ultrasonic sensor such as the ultrasonic probe 1, attenuation of an ultrasonic wave in a body increases as the frequency of the ultrasonic wave increases. Thus, to generate a stronger ultrasonic wave, a high voltage (for example, about 40 V to 200 V) is used for a transmission signal (transmission voltage signal) to be applied to the ultrasonic transducers 21 in ultrasonic transmission. Therefore, a semiconductor element having a high withstand voltage is used in a circuit to which a high voltage of a transmission signal is applied. By contrast, in ultrasonic reception, the ultrasonic transducer 21 receives a weak ultrasonic wave (having an intensity of, for example, about 1% of the transmitted ultrasonic wave) having been attenuated in an object such as the subject 200. Accordingly, the voltage of the reception signal generated by the ultrasonic transducer 21 is small and of orders of magnitude of μV to mV. Therefore, the reception circuit 12 is appropriately operated by a low power supply voltage such as 3 V or 1.2 V. That is, the reception circuit 12 of the ultrasonic sensor can have a circuit configuration of a high frequency bandwidth using a fine semiconductor element.

However, the ultrasonic transducer 21 performs both transmission and reception. Accordingly, in the reception circuit 12 including such a fine semiconductor element, application of a high voltage of a transmission signal to the reception circuit 12 in ultrasonic transmission should be avoided.

Figure 7:
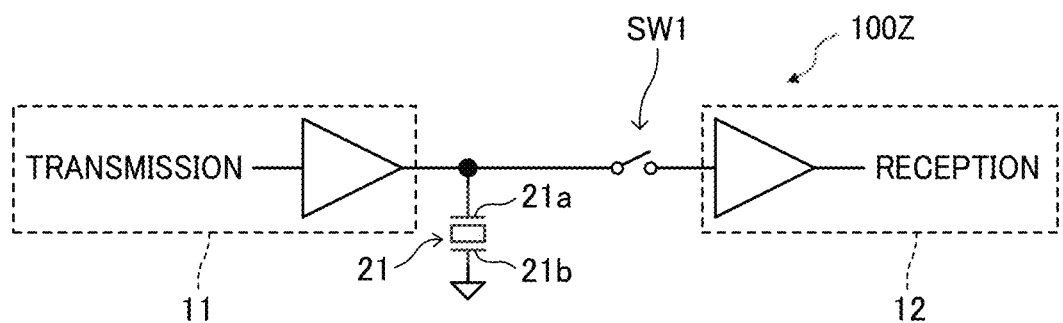
FIG. 7 is a circuit diagram illustrating an ultrasonic sensor including an ultrasonic transducer, a driver that applies a transmission signal, and a reception circuit according to a comparative example.

FIG. 7 is a circuit diagram of a comparative ultrasonic sensor 100Z including the ultrasonic transducer 21, the driver 11 (e.g., a driver circuit) that applies a transmission signal, and the reception circuit 12. In the ultrasonic sensor 100Z, a second terminal 21b of the ultrasonic transducer 21 is grounded, and the driver 11 and the reception circuit 12 are connected to a first terminal 21a of the ultrasonic transducer 21 via a switching element SW1.

The ultrasonic sensor 100Z illustrated in FIG. 7 is described in, for example, Japanese Patent No. 4991722. In the ultrasonic sensor 100Z, in ultrasonic transmission, the switching element SW1 is turned off to electrically separate the reception circuit 12 from the ultrasonic transducers 21, thereby preventing a high voltage of a transmission signal of the driver 11 from being applied to the reception circuit 12. In ultrasonic reception, application of the transmission signal from the driver 11 is turned off, the switching element SW1 is turned on. In this state, the reception circuit 12 detects a reception signal generated at the first terminal 21a of the ultrasonic transducer 21.

In the ultrasonic sensor 100Z illustrated in FIG. 7, a semiconductor element having a high withstand voltage is used in the driver 11 that is connected to the first terminal 21a since a high voltage (for example, 40 V) is applied to the first terminal 21a of the ultrasonic transducer 21 in ultrasonic transmission. As described above, in the driver 11 including a semiconductor element having a high withstand voltage, a parasitic capacitance is relatively large. Therefore, in the ultrasonic sensor 100Z illustrated in FIG. 7, in ultrasonic reception, electric charge generated in the ultrasonic transducer 21 flows into the parasitic capacitance in the driver 11, and the reception signal transmitted to the reception circuit 12 is weakened. As a result, undesirably, the reception sensitivity of the ultrasonic sensor 100Z is lowered.

In the ultrasonic sensor 100Z illustrated in FIG. 7, a weak reception signal generated in the ultrasonic transducers 21 in ultrasonic reception is transmitted to the reception circuit 12 via the switching element SW1. Therefore, undesirably, the S/N ratio of the reception signal transmitted to the reception circuit 12 decreases due to noise in the switching element SW1.

Figure 8:
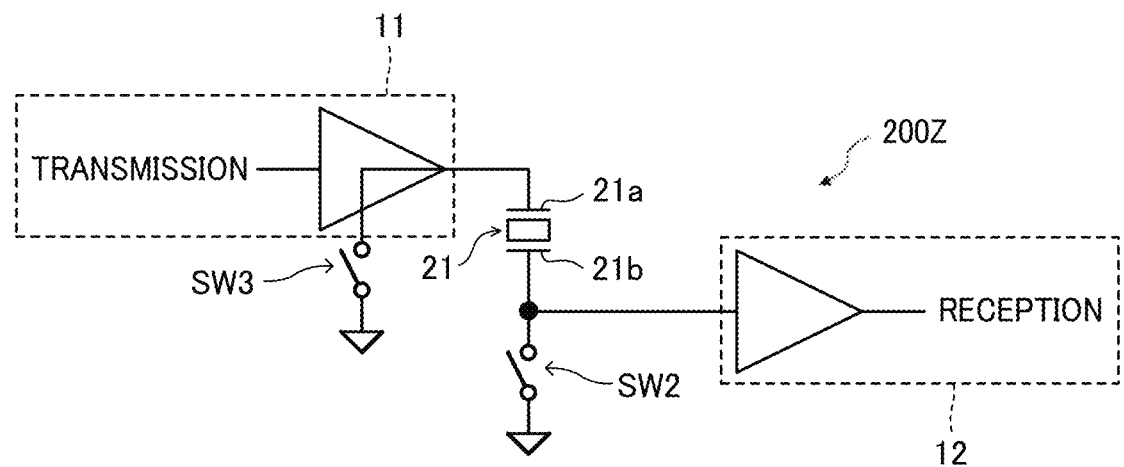
FIG. 8 is a circuit diagram illustrating an ultrasonic sensor including an ultrasonic transducer, a driver, and a reception circuit according to another comparative example.

FIG. 8 is a circuit diagram of another comparative ultrasonic sensor 200Z including the ultrasonic transducer 21, the driver 11, and the reception circuit 12. In the ultrasonic sensor 200Z, the driver 11 is connected to the first terminal 21a of the ultrasonic transducer 21, and the reception circuit 12 is connected to the second terminal 21b of the ultrasonic transducer 21.

The ultrasonic sensor 200Z illustrated in FIG. 8 is described in, for example, Japanese Patent No. 6616296. In the ultrasonic sensor 200Z, the second terminal 21b of the ultrasonic transducer 21 is grounded via a switching element SW2.

In the ultrasonic sensor 200Z illustrated in FIG. 8, in ultrasonic transmission, the switching element SW2 is turned on to keep the second terminal 21b of the ultrasonic transducer 21 at 0 V, so as to prevent application of a high voltage of the transmission signal of the driver 11 to the reception circuit 12. In ultrasonic reception, application of the transmission signal from the driver 11 is stopped, and a switching element SW3 is turned on, to keep the potential of the first terminal 21a of the ultrasonic transducer 21 at 0 V. Further, the switching element SW2 is turned off, to electrically separate the second terminal 21b of the ultrasonic transducer 21 from the ground. Then, the reception circuit 12 detects the reception signal generated at the second terminal 21b of the ultrasonic transducer 21.

In the ultrasonic sensor 200Z illustrated in FIG. 8, the reception circuit 12 is connected to the second terminal 21b of the ultrasonic transducer 21 different from the first terminal 21a to which the driver 11 is connected. This configuration suppresses weakening of the reception signal transmitted to the reception circuit 12 due to the parasitic capacitance of the driver 11 including a semiconductor element having a high withstand voltage. Accordingly, degradation of the reception sensitivity of the ultrasonic sensor 200Z is suppressed.

The ultrasonic sensor 200Z illustrated in FIG. 8 does not includes a switching element between the second terminal 21b of the ultrasonic transducer 21 and the reception circuit 12. Therefore, a weak reception signal generated in the ultrasonic transducer 21 in ultrasonic reception is transmitted to the reception circuit 12 without passing through the switching element. This configuration also eliminates a decrease in the S/N ratio of the reception signal caused by the switching element.

However, in the ultrasonic sensor 200Z illustrated in FIG. 8, the second terminal 21b of the ultrasonic transducer 21 is grounded via the switching element SW2. When the switching element SW2 is a semiconductor element, there is a risk that a voltage out of the allowable voltage range is applied to the reception circuit 12 in ultrasonic transmission.

Figure 9A:
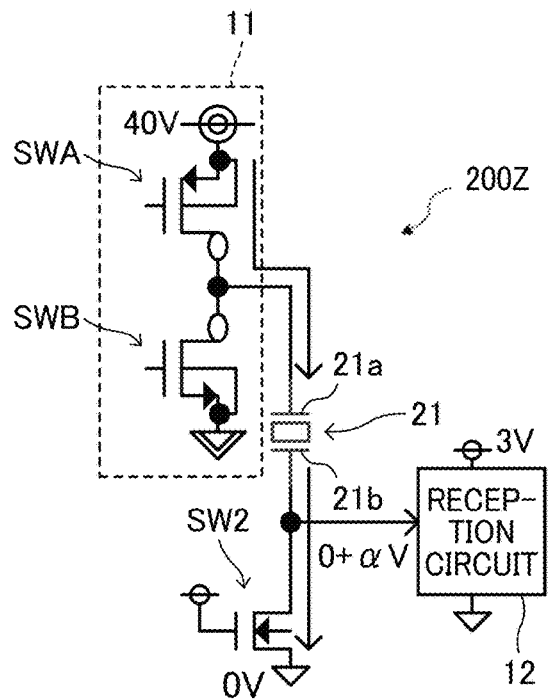
FIGS. 9A and 9B are circuit diagrams illustrating a circuit operation in ultrasonic transmission, performed by the comparative ultrasonic sensor illustrated in FIG. 8.
Figure 9B:
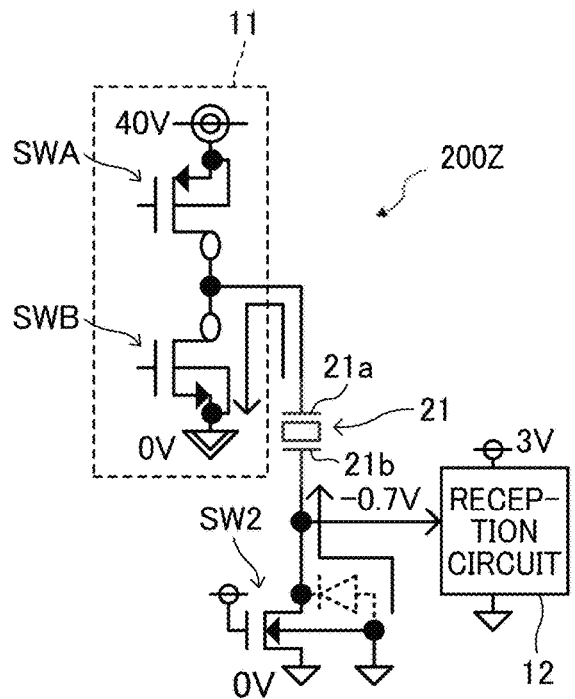

FIGS. 9A and 9B are circuit diagrams illustrating a circuit operation in ultrasonic transmission, performed by the comparative ultrasonic sensor 200Z illustrated in FIG. 8.

In the comparative ultrasonic sensor 200Z illustrated in FIGS. 9A and 9B, the switching element SW2 connected between the second terminal 21b of the ultrasonic transducer 21 and the ground is an n-type metal-oxide semiconductor field-effect transistor (MOSFET). The driver 11 includes complementary metal-oxide-semiconductor field effect transistors (CMOSFETs), specifically, a switching element SWA that is a p-type MOSFET (third MOS transistor) and a switching element SWB that is an n-type MOSFET (fourth MOS transistor). A drain terminal of the switching element SWA (p-type MOSFET) and a drain terminal of the switching element SWB (n-type MOSFET) are connected to the first terminal 21a of the ultrasonic transducer 21. A source terminal of the switching element SWA is supplied with voltage Vdd (for example, 40 V). A source terminal of the switching element SWB is supplied with voltage Vss (for example, 0 V). The driver 11 outputs a transmission signal (transmission voltage signal) by repeatedly turning on and off the switching element SWA (p-type MOSFET) and turning on and off the switching element SWB (n-type MOSFET) according to a predetermined transmission frequency. For example, the predetermined frequency is set experimentally by a manufacturer of the ultrasonic sensor in advance.

As illustrated in FIGS. 9A and 9B, the ultrasonic transducer 21 can be understood as a capacitance model, to be exact, an inductance-capacitance-resistance (LCR) model. In ultrasonic transmission, the switching element SW2 that is an n-type MOSFET is kept on, and the second terminal 21b of the ultrasonic transducer 21 is grounded. Therefore, as illustrated in FIG. 9A, as the switching elements SWA and SWB are turned on and off, a current instantaneously flows through the ultrasonic transducer 21.

At a time when the switching element SWA (p-type MOSFET) is switched from off to on and the switching element SWB (n-type MOSFET) is switched from on to off (at charging), the voltage applied to the first terminal 21a of the ultrasonic transducer 21 is switched from a first low voltage of 0 V to a first high voltage of 40 V. At this time (at charging), as illustrated in FIG. 9A, an instantaneous current flows through the ultrasonic transducers 21 from the first terminal 21a toward the second terminal 21b. This current flows through the switching element SW2 that is an n-type MOSFET toward the ground side. Although the voltage of the second terminal 21b of the ultrasonic transducer 21 is slightly raised by the current flowing through the switching element SW2 that is an n-type MOSFET, the voltage is within a range of 0+α V (α<1 V). The voltage of 0+α V is applied to the reception circuit 12 connected to the second terminal 21b of the ultrasonic transducer 21. Since the voltage of 0+α V has the same polarity as the power supply voltage (3 V) of the reception circuit 12 and is equal to or lower than the power supply voltage, the voltage is within the allowable voltage range of the reception circuit 12 and does not damage or destroy the reception circuit 12.

On the other hand, when the switching element SWA that is a p-type MOSFET is switched from on to off and the switching element SWB that is an n-type MOSFET is switched from off to on (at discharge), the voltage applied to the first terminal 21a of the ultrasonic transducer 21 is switched from the first high voltage of 40 V to the first low voltage of 0 V. At this time (at discharge), as illustrated in FIG. 9B, an instantaneous current flows through the ultrasonic transducer 21 from the second terminal 21b toward the first terminal 21a. This current flows through the switching element SW2 that is an n-type MOSFET from the ground side. The voltage at the second terminal 21b of the ultrasonic transducer 21 is lowered by the current flowing through the switching element SW2 (n-type MOSFET). Accordingly, the voltage at the second terminal 21b is lowered from 0 V to about 0-0.7 V at which the body diode of the switching element SW2 is turned on. Since the voltage of 0-0.7 V (=−0.7 V) has a polarity opposite to that of the power supply voltage (3 V) of the reception circuit 12, the voltage is out of the allowable voltage range of the reception circuit 12 and may damage or destroy the reception circuit 12.

Figure 10A:
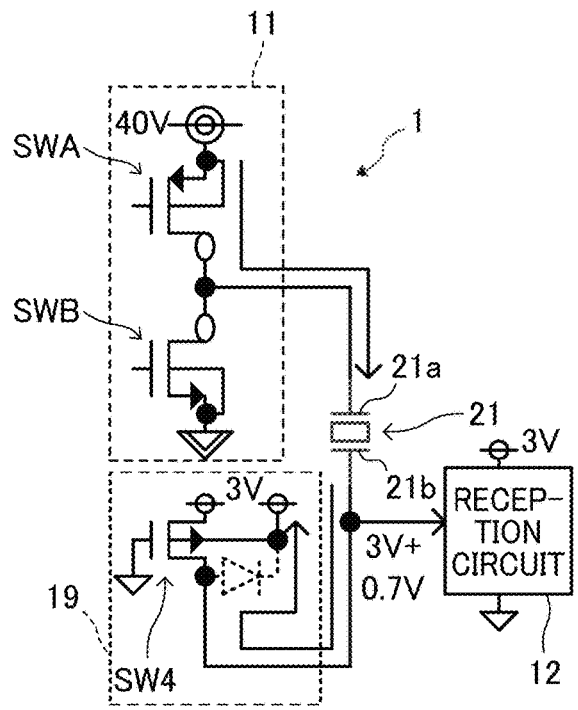
FIGS. 10A and 10B are circuit diagrams illustrating a circuit operation in ultrasonic transmission, performed by the ultrasonic probe serving as an ultrasonic sensor according to one embodiment.
Figure 10B:
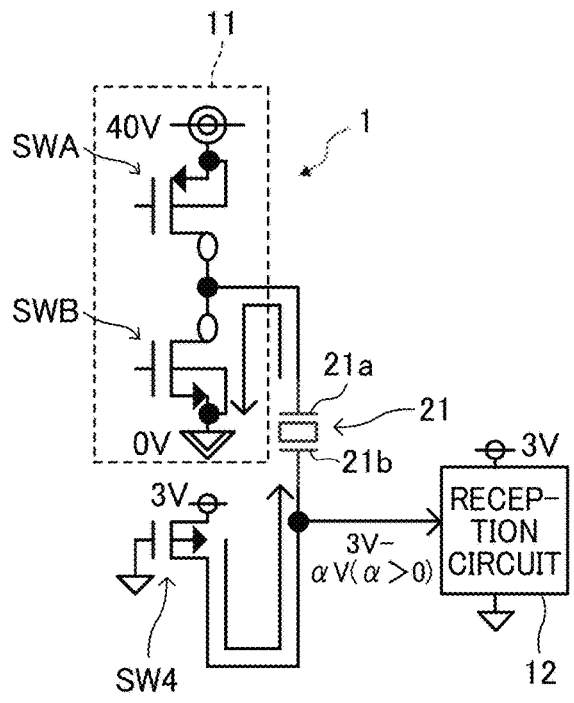

By contrast, referring to FIGS. 10A and 10B, a description is given of a circuit operation at transmission in the ultrasonic sensor serving as the ultrasonic probe 1 according to the present embodiment.

The ultrasonic probe 1 (ultrasonic sensor) according to the present embodiment includes a second voltage output unit 19 connected to the second terminal 21b of the ultrasonic transducer 21 via a switching element SW4 (second switching unit) that is a p-type MOSFET. The second voltage output unit 19 outputs a second high voltage (e.g., 3 V) having the same polarity as the power supply voltage (e.g., 3 V) of the reception circuit 12 and having an absolute value smaller than the first high voltage (e.g., 40 V) applied to the first terminal 21a of the ultrasonic transducer 21. The structures of the driver 11 and the reception circuit 12 are the same as those illustrated in FIGS. 9A and 9B.

In the ultrasonic probe 1 (ultrasonic sensor) of the present embodiment, in ultrasonic transmission, the switching element SW4 is kept on, and the second high voltage (3 V) output from the second voltage output unit 19 is supplied to the second terminal 21b of the ultrasonic transducers 21. Although the power supply voltage of the second voltage output unit 19 of the present embodiment is equal to that of the reception circuit 12, that is, outputs 3 V that is equal to the power supply voltage of the reception circuit 12, the configuration is not limited thereto. Alternatively, the second voltage output unit 19 may output a voltage different from the power supply voltage of the reception circuit 12. For example, the second voltage output unit 19 may output any high voltage having the same polarity as the power supply voltage of the reception circuit 12 and not exceeding the absolute value of the power supply voltage of the reception circuit 12.

At a time when the switching element SWA that is a p-type MOSFET is switched from on to off and the switching element SWB that is an n-type MOSFET is switched from off to on (at discharge), the voltage applied to the first terminal 21a of the ultrasonic transducer 21 is switched from the first high voltage of 40 V to the first low voltage of 0 V. At this time (at discharge), as illustrated in FIG. 10B, an instantaneous current flows through the ultrasonic transducer 21 from the second terminal 21b toward the first terminal 21a. This current flows through the switching element SW4 that is an p-type MOSFET. The current flowing through the switching element SW4 that is a p-type MOSFET slightly lowers the voltage of the second terminal 21b of the ultrasonic transducer 21 from 3 V, but the voltage of the second terminal 21b does not become lower than 0 V. This voltage is equal to or lower than the power supply voltage (3 V) of the reception circuit 12 and within the allowable voltage range of the reception circuit 12. Therefore, the reception circuit 12 is not damaged or broken.

At a time when the switching element SWA (p-type MOSFET) is switched from off to on and the switching element SWB (n-type MOSFET) is switched from on to off (at charging), the voltage applied to the first terminal 21a of the ultrasonic transducer 21 is switched from the first low voltage of 0 V to the first high voltage of 40 V. At this time (at charging), as illustrated in FIG. 10A, an instantaneous current flows through the ultrasonic transducers 21 from the first terminal 21a toward the second terminal 21b. This current flows through the switching element SW4 that is a p-type MOSFET. The current flowing through the switching element SW4 that is a p-type MOSFET raises the voltage at the second terminal 21b of the ultrasonic transducer 21 to about 3+0.7 V at which the body diode of the switching element SW2 is turned on. The voltage of 3+0.7 V (=3.7 V) is greater than the power supply voltage (3 V) of the reception circuit 12, but is within the allowable voltage range of the reception circuit 12. Normally, the allowable voltage range of the reception circuit 12 is equal to or smaller than 1.4 times (4.2 V) the power supply voltage (3 V). Therefore, the reception circuit 12 is not damaged or broken.

Next, a modification of the circuit configuration of the ultrasonic sensor (ultrasonic probe 1) according to the present embodiment will be described.

For speeding up the circuit operation of the reception circuit 12 in order to cope with increases in the frequency of the ultrasonic wave, a fine semiconductor element is used in the reception circuit 12, and the power supply voltage is lowered accordingly. In the present modification, the power supply voltage of the reception circuit 12 is set to 1.2 V, which is lower than 3 V in the above-described embodiment.

Figure 11A:
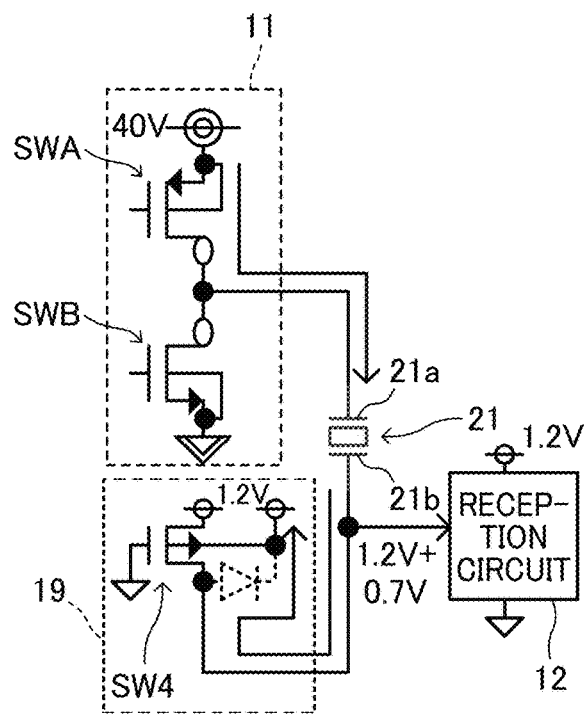
FIGS. 11A and 11B are circuit diagrams illustrating a circuit operation performed by the ultrasonic sensor illustrated in FIGS. 10A and 10B in ultrasonic transmission, when a reception circuit has a power supply voltage of 1.2 V.
Figure 11B:
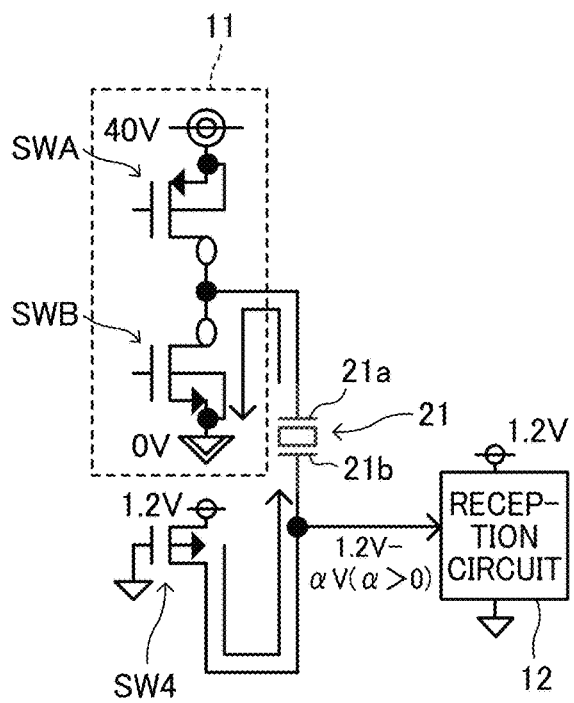

FIGS. 11A and 11B are circuit diagrams illustrating a circuit operation in ultrasonic transmission in a case where the power supply voltage of the reception circuit 12 is set to 1.2 V in the ultrasonic probe 1 (ultrasonic sensor) illustrated in FIGS. 10A and 10B.

Figure 12:
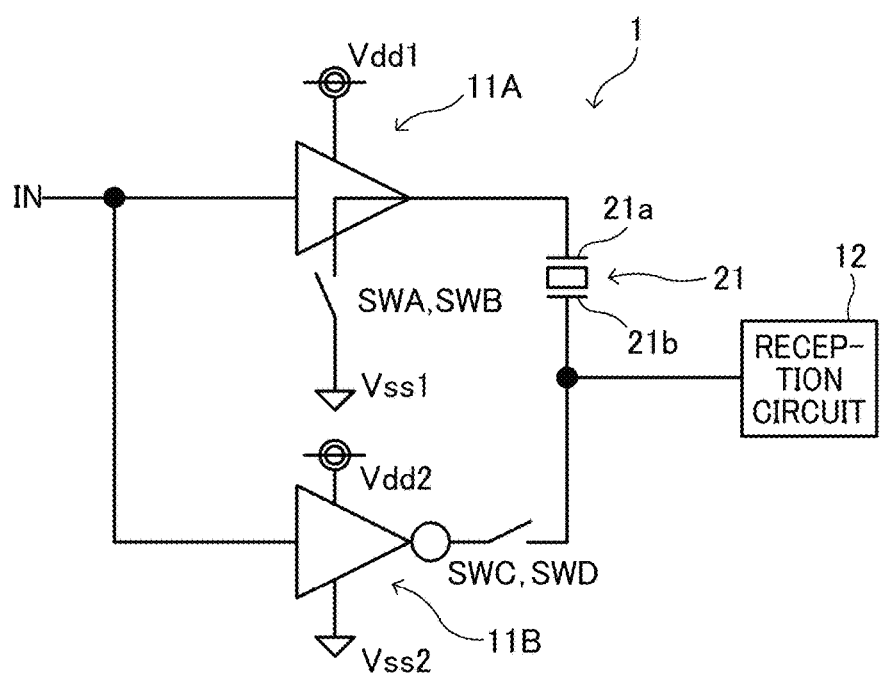
FIG. 12 is a diagram schematically illustrating a circuit configuration of an ultrasonic sensor according to a modification.

FIG. 12 is a diagram schematically illustrating a circuit configuration of the ultrasonic probe 1 (ultrasonic sensor) according to the present modification. In the present modification, the driver 11 includes first and second drive circuits 11A and 11B.

In the case where the power supply voltage of the reception circuit 12 is lowered to 1.2 V, as illustrated in FIG. 11B, when an instantaneous current flows from the second terminal 21b to the first terminal 21a in the ultrasonic transducers 21 (at the time of discharge), the voltage at the second terminal 21b of the ultrasonic transducers 21 is slightly lowered from 1.2 V. Therefore, the reception circuit 12 is not damaged or broken.

However, as illustrated in FIG. 11A, when an instantaneous current flows through the ultrasonic transducers 21 from the first terminal 21a toward the second terminal 21b (at charging), the voltage at the second terminal 21b of the ultrasonic transducers 21 reaches the vicinity of 1.2+0.7 V at which the body diode of the switching element SW2 is turned on. The voltage of 1.2+0.7 V (=1.9 V) is greater than the allowable voltage range (1.68 V) of the reception circuit 12 which is 1.4 times the power supply voltage (1.2 V) of the reception circuit 12. There is a risk that the reception circuit 12 is damaged or broken.

Figure 13:
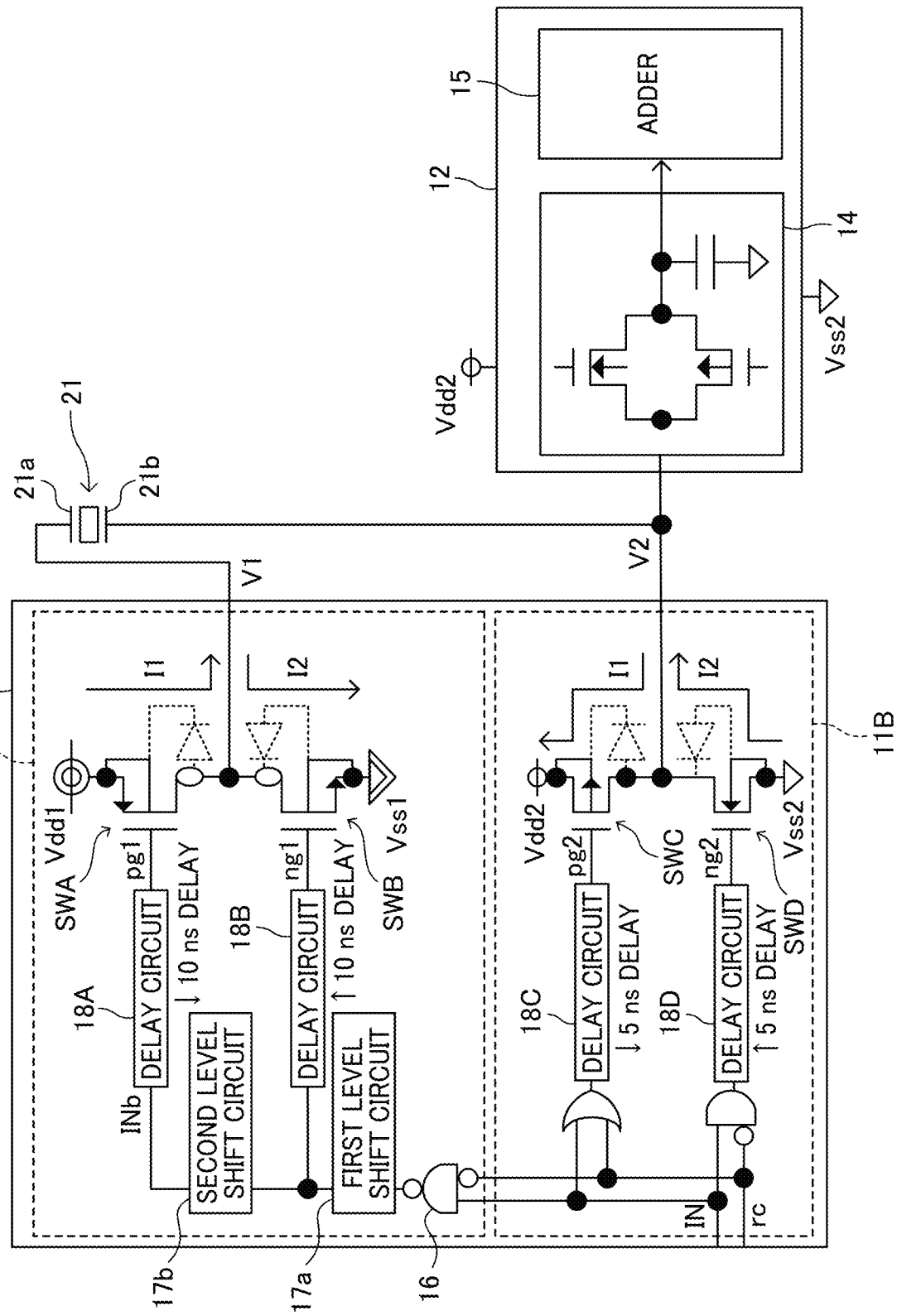
FIG. 13 is a circuit diagram of the ultrasonic sensor illustrated in FIG. 12.

FIG. 13 is a circuit diagram illustrating a detail of the ultrasonic probe 1 (ultrasonic sensor) according to the present modification.

In the driver 11 according to the present modification, the first drive circuit 11A includes the first voltage output unit to output the transmission signal to the first terminal 21a of the ultrasonic transducer 21 and the first switching unit. In the first drive circuit 11A, similar to those illustrated in FIGS. 9A to 11B, the switching element SWA (p-type MOSFET, third MOS transistor) has the source terminal to which a first high voltage (40V) is applied from a power supply Vdd1, the switching element SWB (n-type MOSFET, fourth MOS transistor) has the source terminal to which a first low voltage (0V) is applied from a power supply Vss1, and the drain terminal of the switching element SWA (p-type MOSFET) and the drain terminal of the switching element SWB (n-type MOSFET) are connected to the first terminal 21a of the ultrasonic transducer 21. Hereinafter the first high voltage applied from the power supply Vdd1 is referred to as "voltage Vdd1," and the first low voltage applied from the power supply Vss1 is referred to as "voltage Vss1."

By contrast, in the driver 11 of the present modification, the second voltage output unit and the second switching unit (second drive circuit 11B) for supplying voltage to the second terminal 21b of the ultrasonic transducers 21 have a configuration different from those illustrated in FIGS. 9A to 11B. Specifically, in the second drive circuit 11B, a switching element SWC (p-type MOSFET, first MOS transistor) has a source terminal to which a second high voltage (1.2 V) is applied from a power supply Vdd2, a switching element SWD (n-type MOSFET, second MOS transistor) has a source terminal to which a second low voltage, (ground voltage=0 V) is applied from a power supply Vss2, and a drain terminal of the switching element SWC (p-type MOSFET) and a drain terminal of the switching element SWD (n-type MOSFET) are connected to the second terminal 21b of the ultrasonic transducers 21. Hereinafter the second high voltage applied from the power supply Vdd2 is referred to as "voltage Vdd2," and the second low voltage applied from the power supply Vss2 is referred to as "voltage Vss2."

In the present modification, switching operation between transmission and reception of ultrasonic waves is performed according to an operation switching signal rc.

Specifically, an ultrasonic wave is transmitted when the operation switching signal rc is at the low (L) level, and the ultrasonic wave is received when the operation switching signal rc is at the high (H) level.

Specifically, for transmission of ultrasonic waves, a transmission pulse signal IN corresponding to a predetermined transmission frequency transmitted from the timing generator 13 is input to the driver 11. Since the operation switching signal rc is at the H level, the transmission pulse signal IN input to the driver 11 is input to the second drive circuit 11B as is (second transmission pulse signal IN). The second transmission pulse signal IN input to the second drive circuit 11B is input to a gate terminal pg2 of the switching element SWC (p-type MOSFET) and a gate terminal ng2 of the switching element SWD (n-type MOSFET) via delay circuits 18C and 18D.

On the other hand, the driver 11 further includes an inverter 16 (NOT circuit) that inverts the transmission pulse signal to a first transmission pulse signal INb (inverted signal) to be input to the first drive circuit 11A.

The first transmission pulse signal INb input to the first drive circuit 11A is then input to a gate terminal pg1 of the switching element SWA (p-type MOSFET) and a gate terminal ng1 of the switching element SWB (n-type MOSFET) via first and second level shift circuits 17a and 17b and delay circuits 18A and 18B.

For example, the first and second level shift circuits 17a and 17b function as follows. When the transmission pulse signal IN is a voltage signal that repeatedly oscillates between 1.2 V and 0 V, the first level shift circuit 17a outputs a voltage signal that repeatedly oscillates between 5 V and 0 V, and the second level shift circuit 17b outputs a voltage signal that repeatedly oscillates between 40 V and 35 V.

Each of the delay circuits 18A to 18D delays the changing timing only one of when the input signal changes from the H level to the L level and when the input signal changes from the L level to the H level. For example, the delay circuit 18A delays the changing timing by 10 ns when the input signal changes from the H level to the L level. The delay circuit 18B delays the changing timing by 10 ns when the input signal changes from the L level to the H level. The delay circuit 18C delays the changing timing by 5 ns when the input signal changes from the H level to the L level. The delay circuit 18D delays the changing timing by 5 ns when the input signal changes from the L level to the H level.

In the present modification, in ultrasonic transmission, the first transmission pulse signal INb at the L level is input to the first drive circuit 11A when the transmission pulse signal IN is at the H level. Then, the gate terminals pg1 and ng1 of the switching elements SWA and SWB become the L level. At this time, since the switching element SWA that is a p-type MOSFET is turned on and the switching element SWB that is an n-type MOSFET is turned off, the voltage Vdd1 (40 V) is applied as a voltage V1 (FIG. 13) to the first terminal 21a of the ultrasonic transducer 21.

When the transmission pulse signal IN is at the L level, the first transmission pulse signal INb at the H level is input to the first drive circuit 11A, and the gate terminals pg1 and ng1 of the switching elements SWA and SWB become the H level. At this time, since the switching element SWA that is a p-type MOSFET is turned off and the switching element SWB that is an n-type MOSFET is turned on, the voltage Vss1 (0 V) is applied as the voltage V1 (FIG. 13) to the first terminal 21a of the ultrasonic transducer 21.

Therefore, the first terminal 21a of the ultrasonic transducer 21 is supplied with a transmission voltage signal that oscillates between 40 V and 0 V, in response to switching between the H level and the L level of the transmission pulse signal IN corresponding to the predetermined transmission frequency.

By contrast, in ultrasonic transmission, when the transmission pulse signal IN is at the H level, the second transmission pulse signal IN at the H level is input to the second drive circuit 11B. Then, the gate terminals pg2 and ng2 of the switching elements SWC and SWD are at the H level. At this time, since the switching element SWC that is a p-type MOSFET is turned off and the switching element SWD that is an n-type MOSFET is turned on, the voltage Vss2 (0 V) is applied as a voltage V2 (FIG. 13) to the second terminal 21b of the ultrasonic transducer 21.

On the other hand, when the transmission pulse signal IN is at the L level, the second transmission pulse signal IN at the L level is input to the second drive circuit 11B. Then, the gate terminals pg2 and ng2 of the switching elements SWC and SWD become the L level. At this time, since the switching element SWC that is a p-type MOSFET is turned on and the switching element SWD that is an n-type MOSFET is turned off, the voltage Vdd2 (1.2 V) is applied as the voltage V2 (FIG. 13) to the second terminal 21b of the ultrasonic transducer 21.

Therefore, the second terminal 21b of the ultrasonic transducer 21 is supplied with a transmission voltage signal oscillating between 0 V and 1.2 V, in response to switching between the H level and the L level of the transmission pulse signal IN corresponding to the predetermined transmission frequency.

As described above, in the present modification, in ultrasonic transmission, repeatedly, supply of the voltage Vdd2 (1.2 V) to the second terminal 21b is turned off during a period in which the first high voltage (40 V) is applied from the power supply Vdd1 to the first terminal 21a, and is turned on during a period in which the voltage Vss1 (0 V) is applied to the first terminal 21a. With this operation, with respect to the transmission voltage signal (voltage signal that oscillates between 40 V and 0 V) applied to the first terminal 21a of the ultrasonic transducer 21, a voltage signal (voltage signal that oscillates between 0 V and 1.2 V), which is an inverted signal, is applied to the second terminal 21b of the ultrasonic transducer 21.

In this case, when the voltage applied to the first terminal 21a of the ultrasonic transducer 21 is switched from the first high voltage of 40 V to the first low voltage of 0 V, the voltage applied to the second terminal 21b of the ultrasonic transducer 21 is switched from the second low voltage of 0 V (supply of the second high voltage of 1.2 V is off) to the second high voltage of 1.2 V. At this timing (switching from 40 V to 0 V), as illustrated in FIG. 13, a current I2 instantaneously flows through the ultrasonic transducers 21. As the current I2 flows through the body diode of the switching element SWD (n-type MOSFET) of the second drive circuit 11B, the potential of the second terminal 21b of the ultrasonic transducer 21 is lowered by about 0.7 V.

At this time, in the present modification, the voltage applied to the second terminals 21b of the ultrasonic transducers 21 is switched from the second low voltage of 0 V to the second high voltage of 1.2 V. As a result, the potential of the second terminal 21b of the ultrasonic transducer 21 rises from 0 V. With this configuration, even when the potential of the second terminal 21b of the ultrasonic transducer 21 is lowered by the current I2, the second terminal 21b of the ultrasonic transducer 21 is prevented from having a negative potential. Then, the reception circuit 12 is prevented from being applied with a negative voltage outside the allowable voltage range (a voltage having a polarity opposite to that of the power supply voltage of the reception circuit 12.

Further, in the present modification, when the voltage applied to the first terminal 21a of the ultrasonic transducer 21 is switched from the first low voltage of 0 V to first high voltage of 40 V, the voltage applied to the second terminal 21b of the ultrasonic transducer 21 is switched from the second high voltage of 1.2 V (supply of the second high voltage is on) to the second low voltage of 0 V (supply of the second high voltage is off). At this timing (switching from 0 V to 40 V), as illustrated in FIG. 13, a current I1 instantaneously flows through the ultrasonic transducers 21. As the current I1 flows through the body diode of the switching element SWC (p-type MOSFET) of the second drive circuit 11B, the potential of the second terminal 21b of the ultrasonic transducers 21 is raised by about 0.7 V.

At this time, in the present modification, the voltage applied to the second terminal 21b of the ultrasonic transducer 21 is switched from the second high voltage of 1.2 V to the second low voltage of 0 V. Accordingly, the potential of the second terminal 21b of the ultrasonic transducer 21 lowers from the second high voltage of 1.2 V. As a result, even when the potential of the second terminal 21b of the ultrasonic transducers 21 is raised by the current I1, the potential of the second terminal 21b of the ultrasonic transducer 21 is prevented from rising significantly (approximately 0.7 V) from 1.2 V, and is kept approximately at the second high voltage of 1.2 V or lower.

Therefore, according to the present modification, even in the reception circuit 12 having a low power supply voltage (1.2 V) and including a fine semiconductor element, application of an overvoltage exceeding the allowable voltage range to the reception circuit 12 is prevented, thereby preventing damage or destruction of the reception circuit 12.

In ultrasonic transmission, there is a risk of application of a voltage outside the allowable voltage range to the reception circuit 12 when the switching of the voltage applied to the second terminal 21b of the ultrasonic transducers 21 is delayed from the switching of the voltage applied to the first terminal 21a of the ultrasonic transducers 21.

FIG. 14 is a diagram illustrating the voltages of the first terminal 21a and the second terminal 21b of the ultrasonic transducers 21 when the switching of the voltage applied to the second terminal 21b of the ultrasonic transducers 21 is delayed from the switching of the voltage applied to the first terminal 21a of the ultrasonic transducers 21.

In ultrasonic transmission, the current I1 instantaneously flows through the ultrasonic transducer 21 immediately after the switching of the voltage applied to the first terminal 21a of the ultrasonic transducer 21 from the first low voltage of 0 V to the first high voltage of 40 V, that is, switching of the logical output value of the first terminal 21a in FIG. 14 from the L level to the H level. Then, the potential of the second terminal 21b of the ultrasonic transducer 21 is raised by about 0.7 V as illustrated in FIG. 14. At this time, since the switching of the voltage applied to the second terminal 21b of the ultrasonic transducer 21 is delayed (the logical output value of the second terminal 21b is still at the H level as illustrated in FIG. 14), the second high voltage of 1.2 V is applied to the second terminal 21b of the ultrasonic transducer 21. Therefore, the potential of the second terminal 21b of the ultrasonic transducer 21 is raised from 1.2 V by about 0.7 V, and a voltage of 1.2+0.7 V (1.9 V) is applied to the reception circuit 12. This voltage is greater than the allowable voltage range (1.68 V) of the reception circuit 12 which is 1.4 times the power supply voltage (1.2 V) of the reception circuit 12. There is a risk that the reception circuit 12 is damaged or broken.

Similarly, the current I2 instantaneously flows through the ultrasonic transducer 21 immediately after the switching of the voltage applied to the first terminal 21a of the ultrasonic transducer 21 from the first high voltage of 40 V to the first low voltage of 0 V, that is, switching of the logical output value of the first terminal 21a in FIG. 14 from the H level to the L level. Then, the potential of the second terminal 21b of the ultrasonic transducer 21 is lowered by about 0.7 V. At this time, since the switching of the voltage applied to the second terminal 21b of the ultrasonic transducer 21 is delayed (the logical output value of the second terminal 21b is still at the L level as illustrated in FIG. 14), the second low voltage of 0 V is applied to the second terminal 21b of the ultrasonic transducer 21. Therefore, the potential of the second terminal 21b of the ultrasonic transducer 21 is lowered from 0 V by about 0.7 V, and a voltage of 0−0.7 V (−0.7 V) is applied to the reception circuit 12. There is a risk that voltage having the polarity opposite to that of the power supply voltage (1.2 V) of the reception circuit 12 (voltage outside the allowable voltage range) is applied to the reception circuit 12, which may damage or destroy the reception circuit 12.

FIG. 15 is a diagram illustrating switching times of voltages applied to the second terminal 21b of the ultrasonic transducer 21 in the present modification.

In the ultrasonic transducer 21 according to the present modification, the voltage applied to the second terminal 21b is switched before the voltage applied to the first terminal 21a of the ultrasonic transducer 21 is switched.

In the present modification, in ultrasonic transmission, the voltage applied to the first terminal 21a of the ultrasonic transducer 21 is switched from the first low voltage of 0 V to the first high voltage of 40 V, that is, switching of the logical output value of the first terminal 21a of FIG. 15 from the L level to the H level, after the voltage applied to the second terminal 21b of the ultrasonic transducer 21 is switched from the second high voltage of 1.2 V to the second low voltage of 0 V (after the switching of the logical output value of the second terminal 21b from the H level to the L level as illustrated in FIG. 15). Therefore, the voltage of the second terminal 21b of the ultrasonic transducer 21 has already dropped from 1.2 V toward 0 V. Even if the current I1 flows through the ultrasonic transducer 21, the potential of the second terminal 21b of the ultrasonic transducer 21 does not exceed 1.2 V as illustrated in FIG. 15. Therefore, a voltage exceeding the allowable voltage range is not applied to the reception circuit 12, and damage or breakage of the reception circuit 12 is prevented.

Similarly, in the present modification, in ultrasonic transmission, the voltage applied to the first terminal 21a of the ultrasonic transducer 21 is switched from the first high voltage of 40 V to the first low voltage of 0 V, that is, the logical output value of the first terminal 21a in FIG. 15 is switched from the H level to the L level, after the voltage applied to the second terminal 21b of the ultrasonic transducer 21 is switched from the second low voltage of 0 V to the second high voltage of 1.2 V (after the logical output value of the second terminal 21b is switched from the L level to the H level as illustrated in FIG. 15). Therefore, the voltage of the second terminal 21b of the ultrasonic transducer 21 has already rose from 0 V toward 1.2 V. Even if the current I2 flows through the ultrasonic transducer 21, the potential of the second terminal 21b of the ultrasonic transducer 21 does not drop below 0 V as illustrated in FIG. 15. Therefore, a voltage outside the allowable voltage range is not applied to the reception circuit 12, and the reception circuit 12 is prevented from being damaged or broken.

In the present modification, with such a transmission operation, the first terminal 21a of the ultrasonic transducer 21 is supplied with a transmission voltage signal that oscillates between approximately −0.7 V (=Vss1 (0 V)−0.7 V) and 40.7 V (=Vdd1 (40 V)+0.7 V).

For example, as illustrated in FIG. 15, during a period from when the second terminal 21b switches from the L level to the H level to when the first terminal 21a switches from the H level to the L level, the output voltage of the second voltage output unit changes first. Therefore, the body diode of the switching element SWC (p-type MOSFET) is likely to turn on, and it is possible that a voltage of about 40.7 V is applied to both the switching element SWA and the switching element SWB of the first drive circuit 11A (the first voltage output unit). However, the voltage of 40.7 V is within the allowable voltage range of the switching elements SWA and SWB. The allowable voltage range is normally equal to or lower than 1.4 times the power supply voltage (40 V×1.4=56 V). The switching elements SWA and SWB having such a high withstand voltage are not damaged.

During a period from when the second terminal 21b is switched from the H level to the L level until when the first terminal 21a is switched from the L level to the H level, the output voltage of the second voltage output unit changes first, and thus the body diode of the n-type MOSFET is likely to be turned on. In this case, it is possible that a voltage of about −0.7 V is applied to the switching element SWA and the switching element SWB of the first voltage output unit, but the switching elements SWA and SWB having a high withstand voltage are not damaged.

Figure 16:
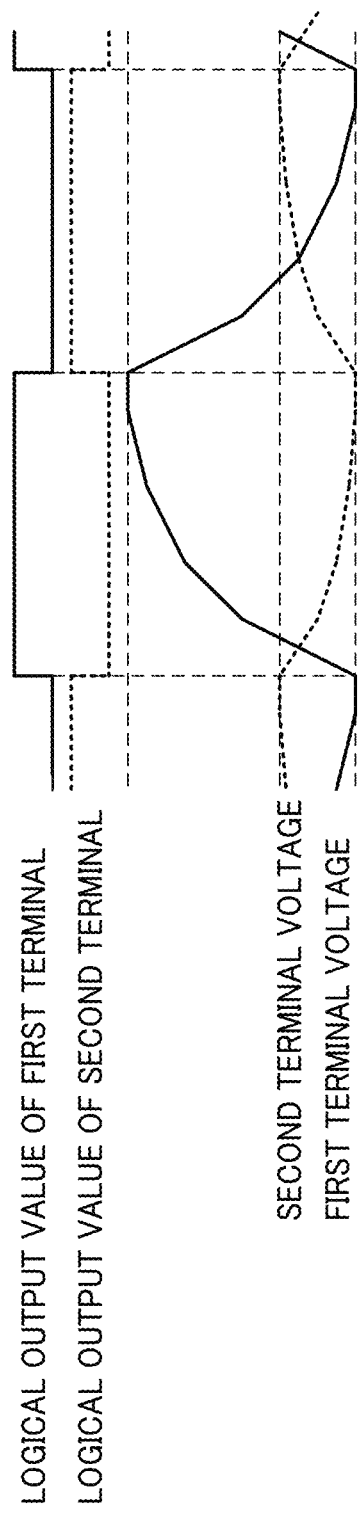
FIG. 16 is a diagram illustrating voltages of first and second terminals of an ultrasonic transducer of the ultrasonic sensor in a case where switching of voltage applied to the second terminal is simultaneous with switching of voltage applied to the first terminal, as a comparative example.

The voltage applied to the second terminal 21b of the ultrasonic transducer 21 may be switched at the same time as the switching of the voltage applied to the first terminal 21a of the ultrasonic transducers 21. As illustrated in FIG. 16, such a configuration also prevents application of a voltage out of the allowable voltage range to the reception circuit 12 and prevents damage or destruction of the reception circuit 12.

However, even when such simultaneous switching is designed, due to some factors, the switching of the voltage applied to the second terminal 21b of the ultrasonic transducer 21 may be delayed from the switching of the voltage applied to the first terminal 21a of the ultrasonic transducers 21.

In such a situation, a voltage outside the allowable voltage range is applied to the reception circuit 12, and the reception circuit 12 may be damaged or broken.

By contrast, in the present modification in which the switching of the voltage applied to the second terminal 21b of the ultrasonic transducer 21 is set prior to the switching of the voltage applied to the first terminal 21a of the ultrasonic transducers 21, delay of the switching of the voltage applied to the second terminal 21b of the ultrasonic transducer 21 from the switching of the voltage applied to the first terminals 21a of the ultrasonic transducers 21 is prevented. Therefore, this configuration stably prevents a voltage outside the allowable voltage range from being applied to the reception circuit 12, and more safely prevents damage or destruction of the reception circuit 12.

Figure 17:
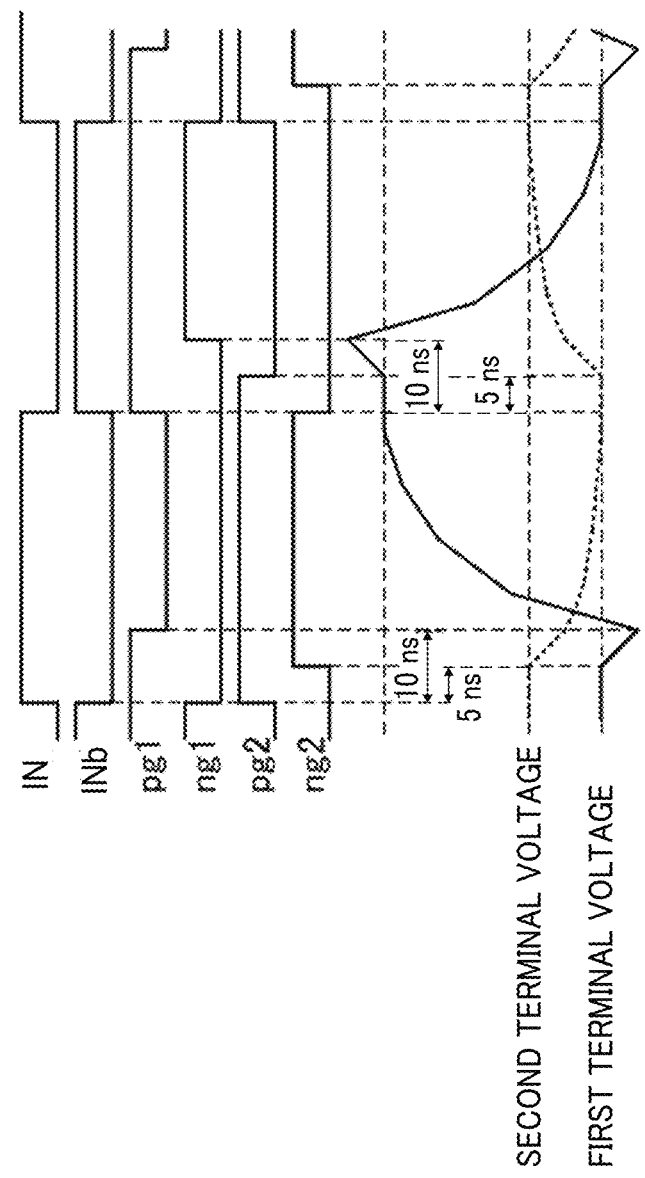
FIG. 17 is a diagram illustrating respective voltage switching of elements of the driver according to the modification.

FIG. 17 is a diagram illustrating voltage switching of the elements of the driver 11 in the present modification.

FIG. 17 illustrates the relationship among the first transmission pulse signal INb, the second transmission pulse signal IN, the gate terminal pg1 of the switching element SWA and the gate terminal ng1 of the switching element SWB in the first drive circuit 11A, the gate terminal pg2 of the switching element SWC and the gate terminal ng2 of the switching element SWD in the second drive circuit 11B, and the voltage of the first terminal 21a and the voltage of the second terminal 21b of the ultrasonic transducers 21. In FIG. 17, for ease of understanding, it is assumed that the delay time of the inverter 16 and the level shift circuits 17a and 17b is 0.

In the first drive circuit 11A, the delay circuits 18A and 18B provide a delay of 10 ns, and there is a period of 10 ns during which the two switching elements SWA and SWB are off.

Similarly, in the second drive circuit 11B, the delay circuits 18C and 18D provide a delay of 5 ns, and there is a period of 5 ns in which the two switching elements SWC and SWD are off. Owing to the delay time difference, in the present modification, the voltage of the second terminal 21b applied from the second drive circuit 11B starts changing in potential for inverting the output logic value earlier by 5 ns than the voltage of the first terminal 21a applied from the first drive circuit 11A.

In the present modification, in ultrasonic reception, one of the switching elements SWA and SWB of the first drive circuit 11A is kept on, and the potential of the first terminal 21a of the ultrasonic transducer 21 is fixed at Vdd1 (=40 V) or Vss1 (=0 V). In the example of FIG. 13, since the operation switching signal rc is at the H level, the potential of the first terminal 21a of the ultrasonic transducer 21 is fixed to Vss1 (=0 V) regardless of the transmission pulse signal IN. On the other hand, since the operation switching signal rc is at the H level, both of the switching elements SWA and SWB of the second drive circuit 11B are kept off regardless of the transmission pulse signal IN. In practice, the second terminal 21b of the ultrasonic transducer 21 is kept at a predetermined potential via a high resistance, and the reception circuit 12 detects a reception signal generated at the second terminal 21b of the ultrasonic transducer 21.

The configurations described above are examples, and various aspects of the present disclosure provide, for example, the following effects, respectively.

Aspect 1

Aspect 1 concerns an ultrasonic sensor (e.g., the ultrasonic probe 1) that applies a transmission voltage signal to a first terminal (the first terminal 21a) of an ultrasonic transducer (e.g., the ultrasonic transducer 21) to control the ultrasonic transducer to transmit an ultrasonic wave to an object (e.g., subject 200) and detects a reception voltage signal generated at a second terminal (the second terminal 21b) of the ultrasonic transducer by the ultrasonic wave reflected by the object. The ultrasonic sensor (the ultrasonic probe 1) includes:

a first voltage output unit (for example, the driver 11 or the first drive circuit 11A) connected to the first terminal of the ultrasonic transducer and configured to output a transmission voltage signal that oscillates between a first high voltage (Vdd1, e.g., 40V) and a first low voltage (Vss1, e.g., 0V) in accordance with a given transmission frequency; and a reception circuit (e.g., the reception circuit 12) connected to the second terminal of the ultrasonic transducer and configured to detect a reception voltage signal generated at the second terminal. The first voltage output unit includes a first switching unit (e.g., the switching elements SWA and SWB) configured to perform switching between supplying the transmission voltage signal output from the first voltage output unit to the first terminal in ultrasonic transmission and maintaining a potential of the first terminal in ultrasonic reception. The ultrasonic sensor further includes a second voltage output unit (19) connected to the second terminal of the ultrasonic transducer and configured to output a second high voltage (Vdd2, e.g., 3 V, 1.2 V) having the same polarity as the power supply voltage (for example, 3 V, 1.2 V) of the reception circuit and having a smaller absolute value than the first high voltage. The second voltage output unit (19) includes a second switching unit (e.g., the switching elements SW4, SWC, and SWD) configured to perform switching between supplying the second high voltage output from the second voltage output unit to the second terminal in ultrasonic transmission and electrically separating the second voltage output unit from the second terminal in ultrasonic reception.

In the comparative ultrasonic sensor described above with reference to FIG. 7, the second terminal of the ultrasonic transducer is grounded, the driver that applies a transmission signal (first voltage output unit) is connected to the first terminal of the ultrasonic transducer, and the reception circuit is connected, via the switching element, to the first terminal of the ultrasonic transducer. The comparative ultrasonic sensor turns off the switching element in ultrasonic transmission, thereby electrically separating the reception circuit from the ultrasonic transducer, so as to prevent application, to the reception circuit, of a high voltage of the transmission voltage signal of the driver circuit. In ultrasonic reception, the application of the transmission voltage signal from the driver circuit is turned off, the switching element is turned on, and the reception circuit detects the reception voltage signal generated at the second terminal of the ultrasonic transducer.

In the ultrasonic sensor, since a high voltage (first high voltage) is applied to the first terminal of the ultrasonic transducer in ultrasonic transmission, a semiconductor element having a high withstand voltage is used in a driver circuit (first voltage output unit) connected to the first terminal. The driver circuit using a semiconductor element having a high withstand voltage has a large parasitic capacitance. Therefore, in the ultrasonic sensor in which the reception circuit is connected to the first terminal of the ultrasonic transducer via the switching element, the electric charge generated in the ultrasonic transducer flows into the parasitic capacitance in the driver circuit in ultrasonic reception, and the reception voltage signal transmitted to the reception circuit is weakened. As a result, the reception sensitivity of the ultrasonic sensor is lowered.

In the ultrasonic sensor in which the reception circuit is connected to the first terminal of the ultrasonic transducer via the switching element, a weak reception voltage signal generated in the ultrasonic transducer in ultrasonic reception is transmitted to the reception circuit via the switching element. Therefore, undesirably, the S/N ratio of the reception voltage signal transmitted to the reception circuit decreases due to the noise of the switching element.

On the other hand, in the ultrasonic sensor according to this aspect, the first voltage output unit is connected to the first terminal (21a) of the ultrasonic transducer, and the reception circuit (12) is connected to the second terminal (21b) of the ultrasonic transducer, similar to the comparative ultrasonic sensor illustrated in FIG. 8. This configuration prevents the reception signal transmitted to the reception circuit from being weakened due to the parasitic capacitance of the first voltage output unit including a semiconductor element having a high withstand voltage and the first switching unit. Accordingly, degradation of the reception sensitivity of the ultrasonic sensor is prevented.

Further, in the ultrasonic sensor according to this aspect, no switching element is present between the second terminal (21b) of the ultrasonic transducer and the reception circuit (12), similar to the comparative ultrasonic sensor illustrated in FIG. 8. Therefore, a weak reception voltage signal generated in the ultrasonic transducer in ultrasonic reception is transmitted to the reception circuit without passing through the switching element. This configuration eliminates a decrease in the S/N ratio of the reception signal caused by the switching element.

In the comparative ultrasonic sensor illustrated in FIG. 8, the second terminal (21b) of the ultrasonic transducer is grounded via a switch. In a case where the switch is a semiconductor element, there is a risk that a voltage out of an allowable voltage range is applied to the reception circuit in ultrasonic transmission.

More specifically, generally, an ultrasonic transducer can be understood as a capacitance model (to be precise, an LCR model). A current instantaneously flows through the ultrasonic transducer when (at charging) the voltage applied to the first terminal (21a) of the ultrasonic transducer switches from the first low voltage (e.g., 0 V) having a small absolute value to the first high voltage (e.g., 40 V) having a large absolute value and when (at discharging) the voltage switches from the first high voltage (e.g., 40 V) to the first low voltage (0 V). At this time, in a configuration in which the switch is, for example, an n-type metal-oxide semiconductor (MOS) transistor (semiconductor element), the potential of the second terminal of the ultrasonic transducer remains within the range of Vss (0 V)+α V even when an instantaneous current flows at the switching (at charging) of the voltage applied to the first terminal of the ultrasonic transducer from the high voltage (40 V) to the low voltage (0 V). However, at the switching (at discharge) from the high voltage (40 V) to the low voltage (0 V), an instantaneous current flows. Then, the potential of the second terminal of the ultrasonic transducer becomes lower than Vss (0 V) and reaches about −0.7 V at which the body diode is turned on. For this reason, a negative voltage (having a polarity opposite to that of the power supply voltage of the reception circuit) outside the allowable voltage range is applied to the reception circuit.

Therefore, in this aspect, the second voltage output unit to output the second high voltage is connected to the second terminal of the ultrasonic transducer. The second high voltage has the same polarity as the power supply voltage of the reception circuit and has an absolute value smaller than that of the first high voltage (output from the first voltage output unit) applied to the first terminal of the ultrasonic transducer. In ultrasonic transmission, the second switching unit supplies the second high voltage output from the second voltage output unit to the second terminal of the ultrasonic transducer. In this configuration, at the switching of the voltage applied to the first terminal of the ultrasonic transducer from the first high voltage to the first low voltage (at discharge), even when an instantaneous current flows, the second terminal of the ultrasonic transducer has a potential lowered by about α V (α<1 V) from the second high voltage. Setting the second high voltage to have an absolute value equal to or greater than α can prevent application of a negative voltage (having a polarity opposite to that of the power supply voltage of the reception circuit) outside the allowable voltage range to the reception circuit in ultrasonic transmission.

However, at the switching of the voltage applied to the first terminal of the ultrasonic transducer from the first low voltage to the first high voltage (at charging), an instantaneous current flows. Then, the potential of the second terminal of the ultrasonic transducer rises from the second high voltage by about 0.7 V. This voltage is applied to the reception circuit. At this time, if the voltage having increased by about 0.7 V from the second high voltage exceeds the allowable voltage range of the reception circuit (for example, a voltage 1.4 times the power supply voltage of the reception circuit), there is a risk that the reception circuit is broken. Therefore, it is preferable that the second high voltage is set to be equal to or higher than α V and within such a range that the voltage increased from the second high voltage by about 0.7 V does not exceed the allowable voltage range of the reception circuit.

In particular, as the absolute value of the second high voltage increases, the difference from the first high voltage decreases, and the transmission voltage signal applied to the ultrasonic transducer becomes weaker. Therefore, it is preferable that the second high voltage is as small as possible.

Aspect 2

According to Aspect 2, in the ultrasonic sensor according to Aspect 1, the second high voltage is substantially the same as a power supply voltage of the reception circuit.

According to this aspect, the configuration of the ultrasonic sensor is simplified as compared with a case where the second high voltage output by the second voltage output unit is different from the power supply voltage of the reception circuit.

Further, in this aspect, as described above, the second voltage output unit and the second switching unit are connected to the second terminal of the ultrasonic transducer to which the reception circuit is connected. Therefore, if the parasitic capacitance due to the semiconductor element of the second voltage output unit or that of the second switching unit is large, in ultrasonic reception, the electric charge generated in the ultrasonic transducer flows into the parasitic capacitance of the second voltage output unit or the second switching unit. Then, the reception voltage signal transmitted to the reception circuit is weakened, resulting in degradation of the reception sensitivity of the ultrasonic sensor. This aspect eliminates such a risk as follows.

In recent years, there has been a demand for higher frequencies of ultrasonic sensors, and accordingly, speeding up of the circuit operation of a reception circuit has been desired. In a case where an integrated circuit that operates in a high frequency band is employed as a reception circuit in order to increase the speed of the circuit operation, a fine semiconductor element is used in the reception circuit. Since the breakdown voltage of each node of the fine semiconductor element is low, the power supply voltage of the reception circuit is low. Therefore, in this aspect, in a case where the frequency of the ultrasonic sensor is increased, the second high voltage applied to the second terminal of the ultrasonic transducer is as small as the power supply voltage of the reception circuit using the fine semiconductor element. If the second high voltage applied to the second terminal of the ultrasonic transducer is as small as the power supply voltage of the reception circuit, a fine semiconductor element can be used for the second voltage output unit that uses the second high voltage and the second switching unit. As a result, the parasitic capacitance of the second voltage output unit and that of the second switching unit are reduced, thereby eliminating the risk of degradation of the reception sensitivity of the ultrasonic sensor.

Aspect 3

According to Aspect 3, in the ultrasonic sensor according to Aspect 1 or 2, the second voltage output unit also outputs a second low voltage having an absolute value smaller than that of the second high voltage. The second switching unit repeatedly performs, in ultrasonic transmission, supply of the second low voltage from the second voltage output unit to the second terminal during a period in which the first high voltage is applied to the first terminal, and supply of the second high voltage from the second voltage output unit to the second terminal during a period in which the first low voltage is applied to the first terminal.

In this aspect, the second terminal of the ultrasonic transducer is supplied with a voltage signal that is an inverted signal of the transmission voltage signal (voltage signal that oscillates between the first high voltage and the first low voltage) applied to the first terminal of the ultrasonic transducer. In this case, at the switching of the voltage applied to the first terminal of the ultrasonic transducer from the first high voltage to the first low voltage (H to L), the voltage applied to the second terminal of the ultrasonic transducer switches from the second low voltage to the second high voltage (L to H). As described above, at the switching of the first high voltage to the first low voltage (H to L), the current instantaneously flows through the ultrasonic transducer, and the potential of the second terminal of the ultrasonic transducer is lowered by about 0.7 V. At this time, in this aspect, since the voltage applied to the second terminal of the ultrasonic transducer is switched from the second low voltage to the second high voltage (L to H), the second terminal of the ultrasonic transducer is prevented from having a negative potential, and application of a negative voltage (voltage having a polarity opposite to that of the power supply voltage of the reception circuit) to the reception circuit is prevented.

Further, in this aspect, at the switching of the voltage applied to the first terminal of the ultrasonic transducer from the first low voltage to the first high voltage (L to H), the voltage applied to the second terminal of the ultrasonic transducer switches from the second high voltage to the second low voltage (H to L). At this time, a current instantaneously flows through the ultrasonic transducer also at the switching (L to H) from the first low voltage to the first high voltage, and the potential of the second terminal of the ultrasonic transducer is raised by about 0.7 V. At this time, in the present aspect, since the voltage applied to the second terminal of the ultrasonic transducer is switched from the second high voltage to the second low voltage (H to L), the potential of the second terminal of the ultrasonic transducer lowers from the second high voltage. Therefore, the potential of the second terminal of the ultrasonic transducer is prevented from rising from the second high voltage by about 0.7 V, and is kept at a potential equal to or lower than the second high voltage. Therefore, even when the reception circuit employs a fine semiconductor element and has a low power supply voltage, application of an overvoltage exceeding the allowable voltage range to the reception circuit is prevented.

Aspect 4

According to Aspect 4, in the ultrasonic sensor according to Aspect 3, in ultrasonic transmission, the second switching unit starts supplying the second low voltage output from the second voltage output unit to the second terminal before the start of application of the first high voltage to the first terminal, and starts supplying the second high voltage output from the second voltage output unit to the second terminal before the start of application of the first low voltage to the first terminal.

At transmission, when the voltage applied to the first terminal of the ultrasonic transducer is switched from the first high voltage to the first low voltage (H to L), a current instantaneously flows through the ultrasonic transducer, and the potential of the second terminal of the ultrasonic transducer is lowered by about 0.7 V. At this time, the voltage applied to the second terminal of the ultrasonic transducer is switched from the second low voltage to the second high voltage (L to H). If this switching is delayed, the second terminal of the ultrasonic transducer has a negative potential, and there is a risk that a negative voltage (voltage having a polarity opposite to that of the power supply voltage of the reception circuit) is applied to the reception circuit.

In this aspect, in ultrasonic transmission, the supply of the second high voltage output from the second voltage output unit to the second terminal starts earlier than the start of application of the first low voltage to the first terminal (H to L). This configuration reliably prevents delay of switching from the second low voltage to the second high voltage from the switching (H to L) of the voltage applied to the first terminal. This configuration reliably prevents application of a negative voltage (voltage having a polarity opposite to that of the power supply voltage of the reception circuit) to the reception circuit.

Similarly, in ultrasonic transmission, when the voltage applied to the first terminal of the ultrasonic transducer is switched from the first low voltage to the first high voltage (L to H), a current instantaneously flows through the ultrasonic transducer, and the potential of the second terminal of the ultrasonic transducer is raised by about 0.7 V. At this time, the voltage applied to the second terminal of the ultrasonic transducer is switched from the second high voltage to the second low voltage (H to L). If this switching is delayed, the potential of the second terminal of the ultrasonic transducer is raised by about 0.7 V from the second high voltage, and there arises a risk that an overvoltage exceeding the allowable voltage range is applied to the reception circuit employing a fine semiconductor element and having a low power supply voltage.

In this aspect, in ultrasonic transmission, the supply of the second low voltage output from the second voltage output unit to the second terminal starts earlier than the start of application of the first high voltage to the first terminal (switching from L to H). Such control reliably prevents delay of the switching from the second high voltage to the second low voltage from the switching from the first low voltage to the first high voltage (L to H). Such control more reliably prevents application of an overvoltage exceeding the allowable voltage range to the reception circuit.

Aspect 5

According to Aspect 5, in the ultrasonic sensor of any one of Aspects 1 to 4, the second switching unit includes: a first MOS transistor (for example, the switching element SWC) in which one of the drain and source terminals is supplied with the second high voltage (Vdd2); and a second MOS transistor (for example, the switching element SWD) in which one of the drain and source terminals is supplied with a ground voltage, and the other of the drain and source terminals of the first MOS transistor and the other of the drain and source terminals of the second MOS transistor are connected to the second terminal of the ultrasonic transducer. In ultrasonic transmission, the second switching unit supplies, to the gate terminals pg2 and ng2, gate voltages for turning on the first MOS transistor and the second MOS transistor, respectively. In ultrasonic reception, the second switching unit supplies, to the gate terminals, gate voltages for turning off the first MOS transistor and the second MOS transistor, respectively.

This configuration enables use of a fine semiconductor element for the second switching unit and reduces the parasitic capacitance of the second switching unit. Accordingly, degradation of the reception sensitivity of the ultrasonic sensor is eliminated.

Aspect 6

According to Aspect 6, in the ultrasonic sensor of Aspect 5, the first voltage output unit includes: a third MOS transistor (for example, the switching element SWA) in which one of the drain and source terminals is supplied with the first high voltage; and a fourth MOS transistor (for example, the switching element SWB) in which one of the drain and source terminals is supplied with the first low voltage, and the other of the drain and source terminals of the third MOS transistor and the other of the drain and source terminals of the fourth MOS transistor are connected to the first terminal of the ultrasonic transducer. The first voltage output unit repeats turning on and off of the third MOS transistor and turning off and on of the fourth MOS transistor according to a predetermined transmission frequency, thereby outputting the transmission voltage signal.

According to this aspect, the first voltage output unit is implemented by the MOS transistors.

Aspect 7

According to Aspect 7, in the ultrasonic sensor of Aspect 6, the first switching unit includes the third MOS transistor and the fourth MOS transistor, repeats turning on and off of the third MOS transistor and turning off and on of the fourth MOS transistor according to a predetermined transmission frequency in ultrasonic transmission, and keeps one of the third MOS transistor and the fourth MOS transistor on in ultrasonic reception, thereby maintaining the potential of the first terminal.

According to this aspect, since the third MOS transistor and the fourth MOS transistor of the first voltage output unit serves as the first switching unit, the configuration is simplified and reduced in size as compared with a case where the first switching unit is a separate component from the first voltage output unit.

Aspect 8

According to Aspect 8, in the ultrasonic sensor of Aspect 6 or 7, the reception circuit includes a MOS transistor, each of the first MOS transistor and the second MOS transistor includes a gate insulating film having a thickness thinner than a thickness of a gate insulating film of each of the third MOS transistor and the fourth MOS transistor and is the same as a thickness of a gate insulating film of the MOS transistor of the reception circuit.

According to this aspect, since a fine semiconductor element can be used for the second switching unit and the parasitic capacitance of the second switching unit can be reduced, deterioration of the reception sensitivity of the ultrasonic sensor is prevented.

Aspect 9

According to Aspect 9, in the ultrasonic sensor of any one of Aspects 6 to 8, the first MOS transistor and the second MOS transistor have a gate channel length shorter than a gate channel length of the third MOS transistor and the fourth MOS transistor.

According to this aspect, since a fine semiconductor element can be used for the second switching unit and the parasitic capacitance of the second switching unit can be reduced, deterioration of the reception sensitivity of the ultrasonic sensor is prevented.

Aspect 10

According to Aspect 10, in the ultrasonic sensor of any one of Aspects 1 to 10, the ultrasonic transducer is a piezoelectric micro-machined ultrasonic transducer (PMUT) or a capacitive micro-machined ultrasonic transducer (CMUT).

According to this aspect, an ultrasonic sensor having a large transmission intensity is realized.

Aspect 11

Aspect 11 concerns an ultrasonic image generating apparatus that includes the ultrasonic sensor according to any one of Aspects 1 to 10, and an image generation unit (for example, the image processor 65) that generates an image based on the reception voltage signal received by the reception circuit of the ultrasonic sensor.

According to this aspect, application of a voltage out of the allowable voltage range to the reception circuit in ultrasonic transmission is prevented, and an appropriate ultrasonic image is generated.

Aspect 12

Aspect 12 concerns an ultrasonic diagnostic apparatus that includes the ultrasonic sensor according to any one of Aspects 1 to 10, and a display (e.g., the display 61) that displays a shape of the object.

According to this aspect, application of a voltage out of the allowable voltage range to the reception circuit at transmission of ultrasonic waves is inhibited, and the shape of the target object is appropriately displayed.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

The invention claimed is:

1. An ultrasonic sensor comprising:
an ultrasonic transducer;
a first voltage output circuit connected to a first terminal of the ultrasonic transducer and configured to output a transmission voltage signal that oscillates between a first high voltage and a first low voltage lower than the first high voltage, in accordance with a transmission frequency, the transmission voltage signal to be supplied to the first terminal of the ultrasonic transducer to control transmission of an ultrasonic wave from the ultrasonic transducer to an object, the first voltage output circuit including a first switch configured to perform switching between:
supplying the transmission voltage signal output from the first voltage output circuit to the first terminal in ultrasonic transmission; and
fixing a potential of the first terminal in ultrasonic reception;
a reception circuit connected to a second terminal of the ultrasonic transducer and configured to detect a reception voltage signal generated at the second terminal by the ultrasonic wave reflected by the object; and
a second voltage output circuit connected to the second terminal of the ultrasonic transducer and configured to output a second high voltage having a same polarity as a power supply voltage of the reception circuit, the second high voltage having an absolute value smaller than an absolute value of the first high voltage, the second voltage output circuit including a second switch configured to perform switching between:
supplying the second high voltage to the second terminal in ultrasonic transmission; and
electrically separating the second voltage output circuit from the second terminal in ultrasonic reception.

2. The ultrasonic sensor according to claim 1,
wherein the second high voltage is equal to the power supply voltage of the reception circuit.

3. The ultrasonic sensor according to claim 1,
wherein the second voltage output circuit further outputs a second low voltage having an absolute value smaller than the absolute value of the second high voltage, and
wherein, in ultrasonic transmission, the second switch repeatedly performs supplying the second low voltage to the second terminal during a period in which the first high voltage is supplied to the first terminal and supplying the second high voltage to the second terminal during a period in which the first low voltage is supplied to the first terminal.

4. The ultrasonic sensor according to claim 3,
wherein, in ultrasonic transmission, the second switch:
starts supplying the second low voltage output to the second terminal prior to start of supplying the first high voltage to the first terminal; and
starts supplying the second high voltage output to the second terminal prior to start of supplying the first low voltage to the first terminal.

5. The ultrasonic sensor according to claim 1,
wherein the second switch includes:
a first metal oxide semiconductor (MOS) transistor in which one of a drain terminal and a source terminal is supplied with the second high voltage; and
a second MOS transistor in which one of a drain terminal and a source terminal is supplied with a second low voltage having an absolute value smaller than the absolute value of the second high voltage,
wherein the other of the drain terminal and the source terminal of the first MOS transistor and the other of the drain terminal and the source terminal of the second MOS transistor are connected to the second terminal of the ultrasonic transducer,
wherein, in ultrasonic transmission, the second switch supplies, to gate terminals of the first MOS transistor and the second MOS transistor, gate voltages for turning on the first MOS transistor and the second MOS transistor, and,
wherein, in ultrasonic reception, the second switch supplies, to the gate terminals of the first MOS transistor and the second MOS transistor, gate voltages for turning off the first MOS transistor and the second MOS transistor.

6. The ultrasonic sensor according to claim 5,
wherein the first voltage output circuit includes:
a third MOS transistor in which one of a drain terminal and a source terminal is supplied with the first high voltage; and
a fourth MOS transistor in which one of a drain terminal and a source terminal is supplied with the first low voltage,
wherein the other of the drain terminal and the source terminal of the third MOS transistor and the other of the drain terminal and the source terminal of the fourth MOS transistor are connected to the first terminal of the ultrasonic transducer, and
wherein the first voltage output circuit repeats turning on and off of the third MOS transistor and turning off and on of the fourth MOS transistor in accordance with the transmission frequency, so as to output the transmission voltage signal.

7. The ultrasonic sensor according to claim 6,
wherein the first switch includes the third MOS transistor and the fourth MOS transistor, and
wherein, in ultrasonic reception, one of the third MOS transistor and the fourth MOS transistor is kept on so as to fix the potential of the first terminal.

8. The ultrasonic sensor according to claim 6,
wherein the reception circuit includes a MOS transistor, and
wherein each of the first MOS transistor and the second MOS transistor includes a gate insulating film having a thickness thinner than a thickness of a gate insulating film of each of the third MOS transistor and the fourth MOS transistor and is same as a thickness of a gate insulating film of the MOS transistor of the reception circuit.

9. The ultrasonic sensor according to claim 6,
wherein each of the first MOS transistor and the second MOS transistor has a gate channel length shorter than a gate channel length of each of the third MOS transistor and the fourth MOS transistor.

10. The ultrasonic sensor according to claim 1,
wherein the ultrasonic transducer is a piezoelectric micromachined ultrasonic transducer or a capacitive micromachined ultrasonic transducer.

11. An ultrasonic image generating apparatus comprising:
the ultrasonic sensor according to claim 1; and
an image processing circuit configured to generate an image based on the reception voltage signal received by the reception circuit of the ultrasonic sensor.

12. An ultrasonic diagnostic apparatus comprising:
the ultrasonic sensor according to claim 1;
an image processing circuit configured to generate an image based on the reception voltage signal received by the reception circuit of the ultrasonic sensor; and
a display configured to display the image generated by the image processing circuit, the image representing a shape of the object.

* * * * *